United States Patent
Sattlegger et al.

(10) Patent No.: US 7,041,662 B2
(45) Date of Patent: May 9, 2006

(54) SUBSTITUTED BENZO [B] AZEPIN-2-ONE COMPOUNDS

(75) Inventors: Michael Sattlegger, Bonn (DE); Helmut Buschmann, Esplugues de Llobregat (ES); Michael Przewosny, Aachen (DE); Werner Englberger, Stolberg (DE); Babette-Yvonne Koegel, Langerwehe-Hamich (DE); Hans Schick, Berlin (DE)

(73) Assignee: Grunenthal GmbH, Aachen (DE)

( * ) Notice: Subject to any disclaimer, the term of this patent is extended or adjusted under 35 U.S.C. 154(b) by 0 days.

(21) Appl. No.: 10/824,244

(22) Filed: Apr. 14, 2004

(65) Prior Publication Data

US 2004/0224938 A1    Nov. 11, 2004

Related U.S. Application Data

(63) Continuation of application No. PCT/EP02/11830, filed on Oct. 23, 2002.

(51) Int. Cl.
*C07D 223/16* (2006.01)
*A61K 31/55* (2006.01)
*A61P 29/00* (2006.01)

(52) U.S. Cl. .................................. 514/212.07; 540/523
(58) Field of Classification Search ................ 540/523; 514/212.07
See application file for complete search history.

(56) References Cited

U.S. PATENT DOCUMENTS 3,475,414 A    10/1969    Havera et al. ........... 260/239.3
5,733,936 A    3/1998    Buschmann et al. ........ 514/646

FOREIGN PATENT DOCUMENTS

WO    WO 93/15059    5/1993

OTHER PUBLICATIONS

Budavari, Susan, et al., "The Merck Index", Merck & Co., Inc., 1989, Nr. 9485, p. 1506.

*Primary Examiner*—Bruck Kifle
(74) *Attorney, Agent, or Firm*—Perman & Green, LLP.

(57) ABSTRACT

The invention relates to substituted benzo[b]azepin-2-one compounds, to methods for the production thereof, to medicaments containing these compounds and to the use of these compounds for producing medicaments.

15 Claims, No Drawings

SUBSTITUTED BENZO [B] AZEPIN-2-ONE COMPOUNDS

This is a continuation of PCT/EP02/11830, filed Oct. 23, 2002.

BACKGROUND OF THE INVENTION

1. Field of the Invention

The present invention relates to substituted benzo[b]azepin-2-one compounds, a process for the production thereof, pharmaceutical preparations containing these compounds and the use of these compounds for the production of pharmaceutical preparations.

2. Brief Description of Related Developments

The treatment of pain is of great medical significance. There is a worldwide need for effective pain treatments. The urgency of the requirement for effective therapeutic methods for providing tailored and targeted treatment of chronic and non-chronic pain, this being taken to mean pain treatment which is effective and satisfactory from the patient's standpoint, is evident from the large number of scientific papers relating to applied analgesia and to basic nociception research which have appeared in recent times.

Conventional opioids, such as for example morphine, are effective in the treatment of severe to very severe pain. However, they produce accompanying symptoms which include respiratory depression, vomiting, sedation, constipation and development of tolerance. Moreover, they are less effective in treating neuropathic or incidental pain, which is in particular frequently experienced by tumour patients.

SUMMARY OF THE INVENTION

The object of the present invention was accordingly to provide new compounds which are suitable as pharmaceutical active ingredients in pharmaceutical preparations, preferably as pharmaceutical active ingredients for combatting pain, preferably chronic or neuropathic pain and may be used for the treatment or prevention of neurodegenerative diseases, preferably Alzheimer's disease, Huntington's chorea or Parkinson's disease, stroke, cerebral infarct, cerebral ischaemia, cerebral oedema, insufficiency states of the central nervous system, preferably hypoxia or anoxia, epilepsy, schizophrenia, psychoses brought about by elevated amino acid levels, AIDS dementia, encephalomyelitis, Tourette's syndrome, perinatal asphyxia, tinnitus, migraine, inflammatory and/or allergic reactions, depression, mental health conditions, urinary incontinence, pruritus or diarrhoea or for anxiolysis or anaesthesia.

According to the invention, this object is achieved by the provision of substituted benzo[b]azepin-2-one-compounds of the general formulae I and II below and in each case of the tautomers thereof, optionally in the form of the diastereomers, pure enantiomers, racemates, non-racemic mixtures of enantiomers or diastereomers and in each case optionally in the form of corresponding bases, salts and solvates, wherein these compounds exhibit in particular an excellent analgesic action.

The present invention therefore provides substituted benzo[b]azepin-2-one compounds of the general formulae I and II and in each case the tautomers thereof,

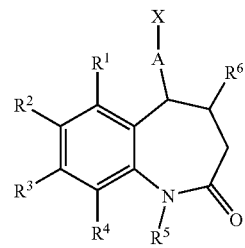

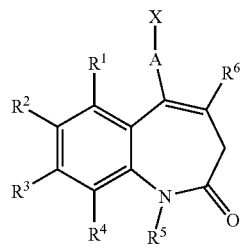

in which $R^1$, $R^2$, $R^3$ and $R^4$, identical or different, denote a linear or branched, saturated or unsaturated aliphatic $C_{1-10}$ residue or a saturated or unsaturated cycloaliphatic $C_{3-7}$ residue, wherein each of the above-stated residues may optionally be joined together via an ether bridge, or hydrogen, a halogen or a hydroxy group, $R^5$ denotes hydrogen, a linear or branched, saturated or unsaturated aliphatic $C_{1-10}$ residue, an aryl or a heteroaryl residue, $R^6$ denotes hydrogen or a residue of the formula —$CH_2$—$NR^7{}_2$, wherein the two residues are identical or different and have the meaning stated below or may form a 3–8-membered ring together with the nitrogen atom connecting them as a ring member, $R^7$ denotes a linear or branched, saturated or unsaturated aliphatic $C_{1-6}$ residue or a saturated or unsaturated cycloaliphatic $C_{3-6}$ residue, A denotes a bridge with one of the following formulae: —$(CH_2)_{n+2}$—, —$(CH_2)_n$—CH=CH—, —$(CH_2)_n$COO—, —$(CH_2)_n$CONH—, —$(CH_2)_{n+1}$O$(CH_2)_p$CO—, —$(CH_2)_{n+1}$O—, —$(CH_2)_{n+1}$NR$^{1'}$— in which n denotes 0, 1, 2 or 3 and p denotes 0 or 1, $R^{1'}$ has the meaning stated hereinafter and the bond to the residue X is always stated last and wherein bonding of the residues $X^{17}$ and $X^{18}$ is possible only via the three bridges stated first, and X denotes one of the following residues of the general formulae $X^1$ to $X^{18}$, in which the unoccupied bond line symbolises the bond to the bridge A and

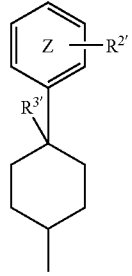

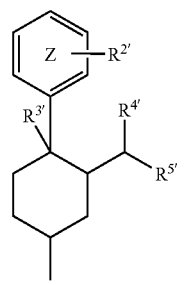 X²
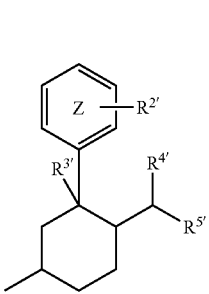 X³
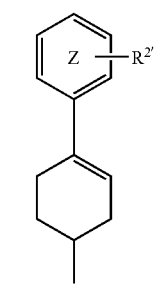 X⁴
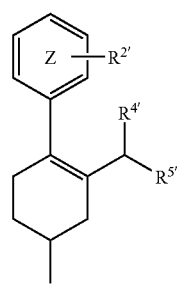 X⁵
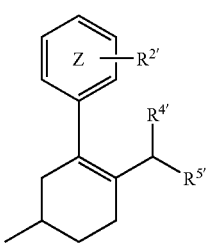 X⁶
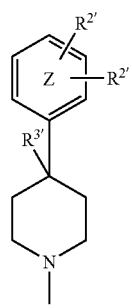 X⁷
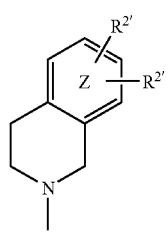 X⁸
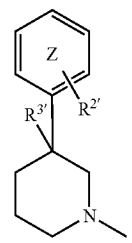 X⁹
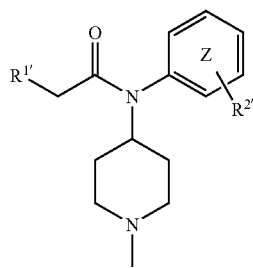 X¹⁰
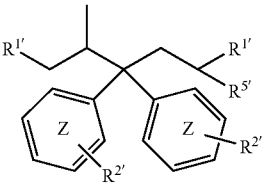 X¹¹
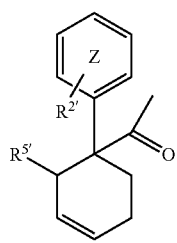 X¹²

-continued

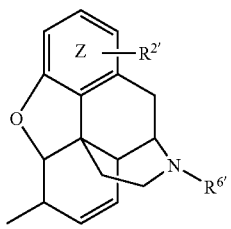
$X^{13}$

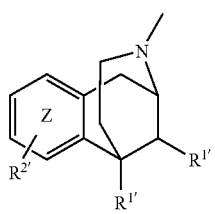
$X^{14}$

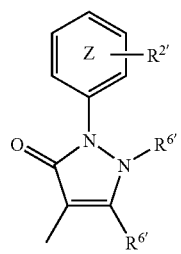
$X^{15}$

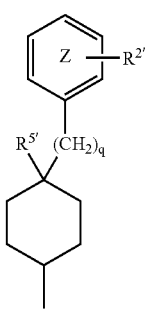
$X^{16}$

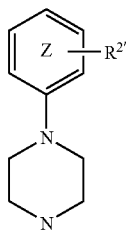
$X^{17}$

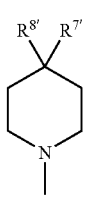
$X^{18}$ in which $R^{1'}$ denotes hydrogen, a linear or branched, saturated or unsaturated aliphatic $C_{1-10}$ residue, a saturated or unsaturated cycloaliphatic $C_{3-7}$ residue, an aryl or heteroaryl residue, $R^{2'}$ denotes a linear or branched, saturated or unsaturated aliphatic $C_{1-10}$ residue, a saturated or unsaturated cycloaliphatic $C_{3-7}$ residue or an aryl or heteroaryl residue wherein all above-stated residues may optionally be joined via an ether, thioether or $SO_2$ bridge, or hydrogen, a halogen, a hydroxy, thiol, cyano or nitro group or a group of the formula —$NR^{1'}_2$ wherein the two residues $R^{1'}$ are identical or different and have the above-stated meaning, $R^{3'}$ denotes a linear or branched, saturated or unsaturated aliphatic $C_{1-10}$ residue, a saturated or unsaturated cycloaliphatic $C_{3-7}$ residue, an aryl or heteroaryl residue, wherein all the above-stated residues may optionally be joined via an ether or an ester bridge, hydrogen, a halogen, a hydroxy group, $R^{4'}$ denotes hydrogen, an aryl or heteroaryl residue, wherein the aryl or heteroaryl residue may comprise at least one substituent $R^{2'}$ with the above meaning, with the exception of hydrogen, $R^{5'}$ denotes a residue of the formula —$NR^{6'}_2$, wherein the two residues $R^{6'}$ may be identical or different and have the meaning stated hereinafter or may form a 3–7-membered ring together with the nitrogen atom connecting them as a ring member, which ring may optionally contain at least one oxygen and/or at least one further nitrogen as a ring atom, wherein the nitrogen may comprise a substituent $R^{10'}$ with the meaning stated hereinafter, $R^{6'}$ denotes a linear or branched, saturated or unsaturated aliphatic $C_{1-6}$ residue, a saturated or unsaturated or cycloaliphatic $C_{3-7}$ residue, an aryl or heteroaryl residue, $R^{7'}$ denotes a cyano, amide or carboxylic acid residue, $R^{8'}$ denotes a residue of the formula —$NR^{9'}_2$, wherein the two residues $R^{9'}$ may be identical or different and have the meaning stated hereinafter or may form a 3–7-membered ring together with the nitrogen atom connecting them as a ring member, which ring may optionally contain at least one oxygen and/or at least one further nitrogen as a ring atom, $R^{9'}$ denotes hydrogen, a linear or branched aliphatic $C_{1-10}$ residue, $R^{10'}$ denotes hydrogen, a linear or branched, saturated or unsaturated aliphatic $C_{1-10}$ residue, an aryl or heteroaryl residue and Z denotes at least one optionally present oxygen, sulfur or nitrogen as a ring atom, and q denotes 0, 1, 2 or 3, optionally in the form of the racemates thereof, the pure stereoisomers thereof, in particular enantiomers or diastereomers, or in the form of mixtures of the stereoisomers, in particular the enantiomers or diastereomers, in any desired mixing ratio or in each case in the form of the acids or bases thereof or in the form of the salts thereof, in particular physiologically acceptable salts, or in the form of the solvates thereof, in particular hydrates.

Tautomers of the compounds of the general formulae I and II arise if $R^5$ denotes hydrogen. Reference is always also made to these possible tautomers.

Substituted benzo[b]azepin-2-one compounds of the general formulae I and II and in each case the tautomers thereof are preferred, in which $R^2$ and $R^3$, identical or different, denote a linear or branched, saturated or unsaturated aliphatic $C_{1-3}$ residue or a halogen and $R^1$ and $R^4$ in each case denote hydrogen, $R^5$ denotes hydrogen or a linear or branched, saturated or unsaturated aliphatic $C_{1-3}$ residue and $R^6$ denotes hydrogen or a residue of the formula —$CH_2$—$NR^7_2$, in which $R^7$ denotes a linear or branched, saturated or unsaturated aliphatic $C_{1-3}$ residue, optionally in the form of the racemates thereof, the pure stereoisomers thereof, in particular enantiomers or diastereomers, or in the form of mixtures of the stereoisomers, in particular the enantiomers or diastereomers, in any desired mixing ratio or in each case in the form of the acids or bases thereof or in the form of the salts thereof, in particular physiologically acceptable salts, or in the form of the solvates thereof, in particular hydrates.

Substituted benzo[b]azepin-2-one compounds of the general formulae I and II and in each case the tautomers thereof are particularly preferred, in which $R^2$ and $R^3$ in each case denote a methyl group or a chlorine and $R^1$ and $R^4$ in each case denote hydrogen, $R^5$ denotes hydrogen or a methyl group and $R^6$ denotes hydrogen or a residue of the formula —$CH_2$—$N(CH_3)_2$, optionally in the form of the racemates thereof, the pure stereoisomers thereof, in particular enantiomers or diastereomers, or in the form of mixtures of the stereoisomers, in particular enantiomers or diastereomers, in any desired mixing ratio or in each case in the form of the acids or bases thereof or in the form of the salts thereof, in particular physiologically acceptable salts, or in the form of the solvates thereof, in particular hydrates.

Substituted benzo[b]azepin-2-one compounds of the general formulae I and II and in each case the tautomers thereof are also preferred, in which $R^3$ denotes a linear or branched, saturated or unsaturated aliphatic $C_{1-3}$ residue or a halogen and $R^1$, $R^2$ and $R^4$ in each case denote hydrogen, $R^5$ denotes hydrogen or a linear or branched, saturated or unsaturated aliphatic $C_{1-3}$ residue and $R^6$ denotes hydrogen or a residue of the formula —$CH_2$—$N(R^7)_2$, in which $R^7$ denotes a linear or branched, saturated or unsaturated aliphatic $C_{1-3}$ residue, optionally in the form of the racemates thereof, the pure stereoisomers thereof, in particular enantiomers or diastereomers, or in the form of mixtures of the stereoisomers, in particular the enantiomers or diastereomers, in any desired mixing ratio or in each case in the form of the acids or bases thereof or in the form of the salts thereof, in particular physiologically acceptable salts, or in the form of the solvates thereof, in particular hydrates.

Substituted benzo[b]azepin-2-one compounds of the general formulae I and II and in each case the tautomers thereof are also particularly preferred, in which $R^3$ denotes a methyl group or a chlorine and $R^1$, $R^2$ and $R^4$ in each case denote hydrogen, $R^5$ denotes hydrogen or a methyl group and $R^6$ denotes hydrogen or a residue of the formula —$CH_2$—$N(CH_3)_2$, optionally in the form of the racemates thereof, the pure stereoisomers thereof, in particular enantiomers or diastereomers, or in the form of mixtures of the stereoisomers, in particular enantiomers or diastereomers, in any desired mixing ratio or in each case in the form of the acids or bases thereof or in the form of the salts thereof, in particular physiologically acceptable salts, or in the form of the solvates thereof, in particular hydrates.

Substituted benzo[b]azepin-2-one compounds of the general formulae I and II and in each case the tautomers thereof are also preferred, in which $R^1$ and $R^3$, identical or different, denote a linear or branched, saturated or unsaturated aliphatic $C_{1-3}$ residue or a halogen and, $R^2$ and $R^4$ in each case denote hydrogen, $R^5$ denotes hydrogen or a linear or branched, saturated or unsaturated aliphatic $C_{1-3}$ residue and $R^6$ denotes hydrogen or a residue of the formula —$CH_2$—$NR^7_2$, in which $R^7$ denotes a linear or branched, saturated or unsaturated aliphatic $C_{1-3}$ residue, optionally in the form of the racemates thereof, the pure stereoisomers thereof, in particular enantiomers or diastereomers, or in the form of mixtures of the stereoisomers, in particular the enantiomers or diastereomers, in any desired mixing ratio or in each case in the form of the acids or bases thereof or in the form of the salts thereof, in particular physiologically acceptable salts, or in the form of the solvates thereof, in particular hydrates.

Substituted benzo[b]azepin-2-one compounds of the general formulae I and II and in each case the tautomers thereof are also particularly preferred, in which $R^1$ and $R^3$ in each case denote a methyl group or a chlorine and $R^2$ and $R^4$ in each case denote hydrogen, $R^5$ denotes hydrogen or a methyl group and $R^6$ denotes hydrogen or a residue of the formula —$CH_2$—$N(CH_3)_2$, optionally in the form of the racemates thereof, the pure stereoisomers thereof, in particular wherein all above-stated groups may optionally be joined via an ether, thioether or $SO_2$ bridge, or hydrogen, a halogen, a hydroxy, thiol, cyano or nitro group or a group of the formula —$NR1'_2$ wherein the two groups $R^{1'}$ are identical or different and have the above-stated meaning, $R^{3'}$ denotes a linear or branched, saturated or unsaturated aliphatic $C_{1-10}$ group, a saturated or unsaturated cycloaliphatic $C_{3-7}$ group, or an aryl group, wherein all the above-stated group may optionally be joined via an ether or an ester bridge, hydrogen, a halogen, a hydroxy group, $R^{4'}$ denotes hydrogen, or an aryl group, wherein the aryl group may comprise at least one substituent $R^{2'}$ with the above meaning, with the exception of hydrogen, $R^{5'}$ of the formula —$NR^{6'}_2$, wherein the two $R^{6'}$ may be identical or different and have the meaning stated hereinafter or may form a 3–7-membered ring together with the nitrogen atom connecting them as a ring member, which ring may optionally contain at least one oxygen and/or at lease one further nitrogen as a ring atom, wherein the nitrogen may comprise a substituent $R^{10'}$ with the meaning stated hereinafter, $R^{6'}$ denotes a linear or branched, saturated or unsaturated aliphatic $C_{1-6}$ group, a saturated or unsaturated cycloaliphatic $C_{3-7}$ group, or an aryl group, enantiomers or diastereomers, or in the form of mixtures of the stereoisomers, in particular enantiomers or diastereomers, in any desired mixing ratio or in each case in the form of the acids or bases thereof or in the form of the salts thereof, in particular physiologically acceptable salts, or in the form of the solvates thereof, in particular hydrates.

Also preferred are substituted benzo[b]azepin-2-one compounds of the general formulae I and II and in each case the tautomers thereof, in which A denotes a bridge of the formula —$CH_2$—COO— or —$CH_2$CONH— optionally in form of the racemates thereof, the pure stereoisomers thereof, in particular enantiomers or diastereomers, or in the form of mixtures of the stereoisomers, in particular the enantiomers or diastereomers, in any desired mixing ratio or in each case in the form of the acids or bases thereof or in the form of the salts thereof, in particular physiologically acceptable salts, or in the form of the solvates thereof, in particular hydrates.

Also preferred are substituted benzo[b]azepin-2-one compounds of the general formulae I and II and in each case the tautomers thereof, in which X denotes a residue of the following formula:

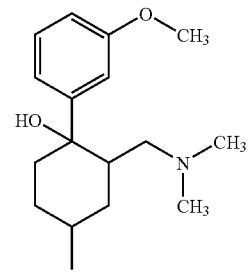

optionally in the form of the racemates thereof, the pure stereoisomers thereof, in particular enantiomers or diastereomers, or in the form of mixtures of the stereoisomers, in particular the enantiomers or diastereomers, in any desired mixing ratio or in each case in the form of the acids or bases thereof or in the form of the salts thereof, in particular physiologically acceptable salts, or in the form of the solvates thereof, in particular hydrates.

The following substituted benzo[b]azepin-2-one compounds and optionally the tautomers thereof are very particularly preferred:

2'-(8-Chloro-2-oxo-2,3-dihydro-1H-benzo[b]azepin-5-yl) acetic acid [3"-(N,N-dimethylaminomethyl)-4"-hydroxy-4"-(m-methoxyphenyl)cyclohexyl]ester, 2'-(8-Chloro-1-methyl-2-oxo-2,3-dihydro-1H-benzo[b]azepin-5-yl) acetic acid [3"-(N,N-dimethylaminomethyl)-4"-hydroxy-4"-(m-methoxyphenyl)cyclohexyl]ester, 2'-(8-Chloro-2-oxo-2,3-dihydro-1H-benzo[b]azepin-5-yl)-N-[3"-(N,N-dimethylaminomethyl)-4"-hydroxy-4"-(m-methoxyphenyl)cyclohexyl]acetamide, 2'-(8-Chloro-1-methyl-2-oxo-2,3-dihydro-1H-benzo[b]azepin-5-yl)-N-[3"-(N,N-dimethylaminomethyl)-4"-hydroxy-4"-(m-methoxyphenyl)cyclohexyl]acetamide optionally in the form of the racemates thereof, the pure stereoisomers thereof, in particular enantiomers or diastereomers, or in the form of mixtures of the stereoisomers, in particular the enantiomers or diastereomers, in any desired mixing ratio or in each case in the form of the acids or bases thereof or in the form of the salts thereof, in particular physiologically acceptable salts, or in the form of the solvates thereof, in particular hydrates.

The present invention also provides a process for the production of substituted benzo[b]azepin-2-one compounds of the above-stated general formulae I and II and in each case the tautomers and corresponding stereoisomers thereof, characterised in that A) an optionally substituted 2-aminobenzoic acid alkyl ester of the general formula (1), in which $R^1$, $R^2$, $R^3$, $R^4$ and $R^5$ have the above-stated meaning and R denotes an alkyl group, preferably a methyl or ethyl group,

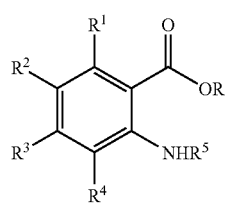

(1)

is reacted with succinic acid dialkyl ester of the general formula (2), in which R' denotes an alkyl group, preferably a methyl or ethyl group and $R^x$ denotes chlorine or an alkoxy group, preferably a methoxy or ethoxy group,

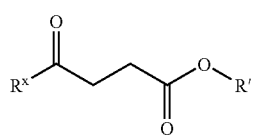

(2)

under suitable reaction conditions, in a suitable solvent, preferably pyridine, and then worked up, optionally followed by purification of the optionally substituted N-(2-carbalkoxyphenyl)succinic acid alkyl ester amide formed of the general formula (3), in which R, R', $R^1$ $R^2$, $R^3$, $R^4$ and $^5$ have the above-stated meaning,

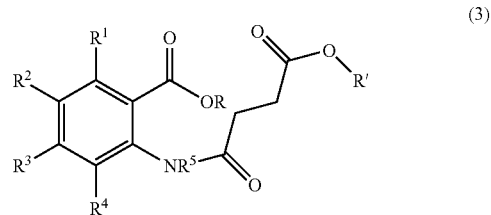

(3)

B) an optionally substituted N-(2-carbomethoxyphenyl)succinic acid alkyl ester amide of the general formula (3) is reacted in the presence of potassium tert-butanolate in a suitable solvent and then worked up, optionally followed by purification of the optionally substituted 5-hydroxy-2-oxo-2,3-dihydro-1H-benzo[b]azepin-4-carboxylic acid alkyl ester formed of the general formula (4), in which R', $R^1$, $R^2$, $R^3$, $R^4$ and $R^5$ have the above-stated meaning,

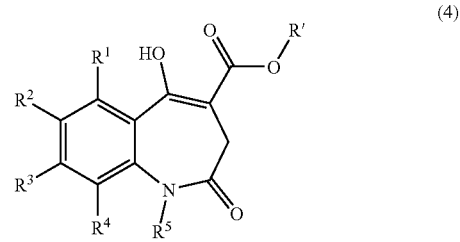

(4)

C) an optionally substituted 5-hydroxy-2-oxo-2,3-dihydro-1H-benzo[b]azepin-4-carboxylic acid alkyl ester of the general formula (4) is reacted in a dimethyl sulfoxide/water mixture at elevated temperature and then worked up, optionally followed by purification of the optionally substituted 2,3,4,5-tetrahydro-1H-benzo[b]azepin-2,5-dione of the general formula (5), in which $R^1$, $R^2$, $R^3$ $R^4$ and $^5$ have the above-stated meaning,

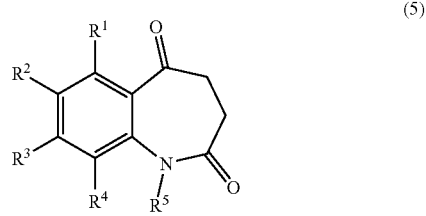

(5)

D) an optionally substituted 2,3,4,5-tetrahydro-1H-benzo[b]azepin-2,5-dione of the general formula (5) is reacted with a substituted aminomethylene hydrochloride of the general formula (6), in which the residue $R^7$ has the above-stated meaning,

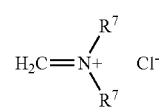

(6)

in the presence of an acid, preferably acetyl chloride, in a suitable solvent, preferably acetonitrile, and then worked up, optionally followed by purification of the optionally substituted aminomethyl-2,3,4,5-tetrahydro-1H-benzo[b] azepin-2,5-dione of the general formula (7), in which $R^1$, $R^2$, $R^3$, $R^4$, $R^5$ and $R^7$ have the above-stated meaning,

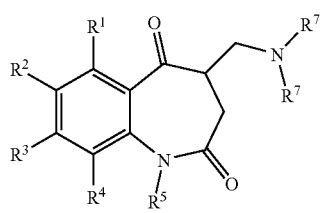

(7)

E) an optionally substituted 2,3,4,5-tetrahydro-1H-benzo[b] azepin-2,5-dione of the general formula (8), in which $R^1$, $R^2$, $R^3$, $R^4$, $R^5$ and $R^6$ have the above-stated meaning and which dione combines the compounds of the general formulae (5) and (7),

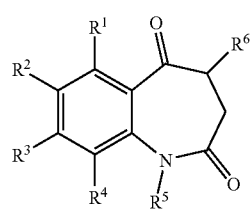

(8)

is reacted with a phosphonoalkanoic acid trialkyl ester of the general formula (9), in which n has the above-stated meaning and R″ denotes an alkyl group, preferably a methyl or ethyl group,

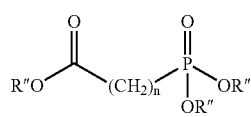

(9)

in the presence of a base, preferably potassium tert-butanolate, in a suitable solvent, preferably dimethylformamide, and then worked up, optionally followed by purification of the compound formed of the formula Y—COOR″, in which R″ has the above-stated meaning and Y denotes a residue of the general formula Y, in which the unoccupied bond line symbolises the bond to the residue —COOR″ and

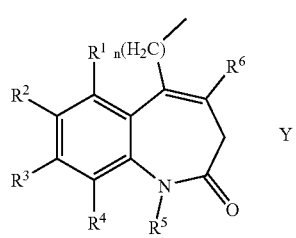

in which $R^1$, $R^2$, $R^3$, $R^4$, $R^5$, $R^6$ and n have the above-stated meaning, F) optionally an ester of the formula Y—COOR″ is reacted in the presence of a base, preferably sodium or potassium hydroxide, in a suitable solvent, preferably an alcohol/water mixture, and then worked up, optionally followed by purification of the carboxylic acid formed of the formula Y—COOH, in which Y has the above-stated meaning, G) optionally a carboxylic acid of the formula Y—COOH or a carboxylic acid ester of the formula Y—COOR″, in which Y and R″ have the above-stated meaning, is derivatised, in that
  a) a carboxylic acid or carboxylic acid ester of the formula Y—COOH or Y—COOR″ is reduced with the assistance of reducing agents, preferably lithium aluminium hydride, in a suitable solvent, preferably tetrahydrofuran, to the corresponding alcohol of the formula Y—CH₂—OH,
  b) a carboxylic acid or carboxylic acid ester of the formula Y—COOH or Y—COOR″ is reduced with the assistance of reducing agents, preferably diisobutylaluminium hydride, in a suitable solvent, preferably hexane, to the corresponding aldehyde of the formula Y—CHO or
  c) an alcohol of the formula Y—CH₂—OH according to a) is reacted with a brominating agent, preferably PBr₃ or Ph₃PBr₂ (with Ph denoting phenyl residue) to yield the corresponding bromide of the formula Y—CH₂—Br
  and then worked up and the product is optionally purified, H) a compound of the formula $X^1$—$R^{IV}$, in which $X^1$ has the above-stated meaning and $R^{IV}$ denotes a functional group, is optionally produced in that
  a) 1,4-cyclohexanedione monoethylene ketal, 4-aminocyclohexan-1-one ethylene ketal or 4-oxocyclohexane carboxylic acid is reacted with magnesium and a brominated or chlorinated, optionally substituted aromatic or heteroaromatic compound in a suitable solvent, preferably dry diethyl ether, at elevated temperature to yield the corresponding coupling product and then the ketal is optionally cleaved by reaction with hydrochloric acid in a suitable solvent, preferably tetrahydrofuran and worked up, optionally followed by purification of the product of the formula $X^{1a}$=O, $X^{1a}$—NHR¹' or $X^{1a}$—CO₂H, in which $X^{1a}$ denotes a residue of the formula $X^{1a}$ and R¹', R²' and Z have the above-stated meaning and the unoccupied bond line symbolises the bond to the residue =O, —NHR¹' or —CO₂H,

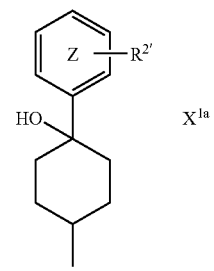

b) optionally a ketone of the formula $X^{1a}$=O is reacted in the presence of a suitable reducing agent, preferably sodium borohydride, in a suitable solvent, preferably methanol, to yield the corresponding alcohol of the formula $X^{1a}$—OH, worked up and the product is optionally purified, c) optionally a ketone of the formula X¹ª=O is reacted under nitrogen in a suitable solvent, preferably tetrahydrofuran, firstly with ammonium trifluoroacetate and then with glacial acetic acid and sodium triacetoxyborohydride, to yield the corresponding amine of the formula X¹ª—NH₂, worked up and the product is optionally purified, d) optionally a carboxylic acid of the formula X¹ª=CO₂H is activated by reaction with dicyclohexylcarbodiimide or by conversion into the carboxylic acid chloride or a mixed anhydride, reacted with diazomethane in a suitable solvent, preferably ether, and then treated with water, worked up and the product of the formula X¹ª—CO—CH₂—OH is optionally purified, e) optionally the hydroxy group in position 4 of the cyclohexane ring in the residue X¹ª is converted into hydrogen, a halogen, an ether, ester, alkyl, aryl or heteroaryl group, in that α) in order to introduce an ether group, a compound from one of steps a)–d) is reacted with an aliphatic or cycloaliphatic compound in the presence of a suitable catalyst in a suitable solvent, preferably in the presence of sodium hydride in dimethylformamide or in the presence of potassium hydroxide in dimethyl sulfoxide, or with an alkylating agent in a suitable solvent, preferably with a diazo compound in diethyl ether, or with an aryl or heteroaryl compound in the presence of diethylazo dicarboxylate and triphenylphosphine, β) in order to introduce a halogen, a compound from one of steps a)–d) is reacted with a halogenating agent in a suitable solvent, preferably with POCl₃ in dimethylformamide, with PPh₃/Cl₂, with PPh₃/Br₂, with triphenylphosphine/n-chlorosuccinimide or with HCl/ZnCl₂, γ) in order to introduce a hydrogen, a compound from step β) is reacted with hydrogen in the presence of a suitable catalyst, preferably palladium/carbon, in a suitable solvent, δ) in order to introduce an aliphatic or cycloaliphatic residue or an aryl or heteroaryl group, a compound from step β) is reacted with an aliphatic or cycloaliphatic boronic acid or a boronic acid ester or an aryl or heteroaryl borodihydroxide compound in the presence of palladium(II) acetate and potassium carbonate in a suitable solvent, preferably a dimethylformamide/water mixture, or ε) in order to introduce an ester group, a compound from one of steps a)–d) is reacted with a carboxylic acid chloride in the presence of a suitable catalyst in a suitable solvent and then worked up, optionally followed by purification of the compound formed of the formula $X^1$—$R^{IV}$, in which $X^1$ denotes the formula $X^1$

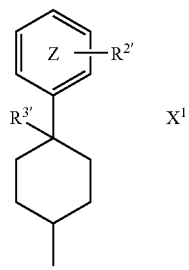

and $R^{IV}$, $R^2$ and $R^3$ have the above-stated meaning,

I) a compound of the formula X—$R^{IV}$, in which X has the above-stated meaning and $R^{IV}$ denotes a functional group, is optionally derivatised in that a) a ketone of the formula X=O is reacted 1) with methoxymethyl triphenylphosphinium chloride under protective gas in a suitable solvent, preferably in dimethylformamide, in the presence of sodium hydride and then with hydrochloric acid or 2) with Me₃S⁺BF₄⁻ to yield the corresponding aldehyde X—CHO extended by one carbon atom, b) an aldehyde of the formula X—CHO according to a) is reacted with a reducing agent, preferably sodium borohydride, in a suitable solvent, preferably an ethanol/water mixture, to yield the corresponding alcohol X—CH₂—OH, c) an alcohol C—CH₂—OH according to b) or of the formula X—OH is reacted with a brominating agent, preferably triphenylphosphine dibromide, in a suitable solvent, preferably acetonitrile, to yield the corresponding bromide of the formula X—CH₂—Br or X—Br, d) a bromide of the formula X—CH₂—Br according to c) is reacted with a phosphine of the formula $PR^V_3$, in which $R^V$ denotes an organic residue, preferably a phenyl residue, in a suitable solvent, preferably toluene, ether, tetrahydrofuran or acetone, with cooling and under protective gas to yield the corresponding phosphonium salt $R^V_3P^+$—CHX⁻ or e) a bromide of the formula X—CH₂—Br according to c) is reacted with a phosphite of the formula HP(O)(OR^{VI})₂, in which $R^{VI}$ denotes an organic residue, at elevated temperature, preferably 200° C., to yield the corresponding phosphonate $(R^{VI}O)_2P(O)$—CH₂—X and then worked up and the product is optionally purified, J) a compound from step F) or G), in which Y has the above-stated meaning, is reacted with a compound of the formula $X^1$—$R^{IV}$ from step H) or a compound X—$R^{IV}$ from step I), in which X, $X^1$ and $R^{IV}$ have the above-stated meaning, in that a) a carboxylic acid of the formula Y—COOH is reacted with an amine of the formula X—NH₂ in the presence of a suitable condensing agent, preferably dicyclohexylcarbodiimide, 1-hydroxybenzotriazole and N-methylmorphine, in a suitable solvent, preferably dimethylformamide, with formation of an amide bridge, b) a carboxylic acid of the formula Y—COOH is reacted with an alcohol of the formula X—OH in the presence of a suitable condensing agent in a suitable solvent with formation of an ester bridge, the reaction preferably taking place in the presence of methylimidazole and 1-(mesitylene-2'-sulfonyl)-3-nitro-1,2,4-triazole in tetrahydrofuran or in the presence of dicyclohexylcarbodiimide, 1-hydroxybenzotriazole and N-methylmorphine in dimethylformamide, c) a bromide of the formula Y—CH₂—Br is reacted with a compound of the formula X—CO(CH₂)p-OH, in which p has the above-stated meaning, under protective gas in the presence of a suitable catalyst, preferably sodium hydride or potassium tert-butylate, in a suitable solvent, preferably dimethylformamide, with formation of a bridge of the formula —CO(CH₂)$_p$—O—CH₂—, d) an alcohol of the formula Y—CH₂—OH is reacted with a bromide of the formula X—Br under protective gas in the presence of a suitable condensing agent, preferably sodium hydride or potassium tert-butylate, in a suitable solvent, preferably dimethylformamide, with formation of an ether bridge, e) a bromide of the formula Y—CH$_2$—Br is reacted with an alcohol of the formula X—OH under protective gas in the presence of a suitable condensing agent, preferably sodium hydride or potassium tert-butylate, in a suitable solvent, preferably dimethylformamide, with formation of an ether bridge, f) an aldehyde of the formula Y—CHO is reacted with an amine of the formula X—NHR$^{1'}$ in the presence of a suitable reducing agent, preferably sodium cyanoborohydride and sodium triacetoxyborohydride, in a suitable solvent, preferably a mixture of tetrahydrofuran and 1,2-dichloroethane, with formation of an amino bridge, g) an aldehyde of the formula Y—CHO is reacted with a phosphonium salt R$^V_3$P$^+$—CHX$^-$, in which R$^V$ has the above-stated meaning, under protective gas in the presence of suitable catalysts in a suitable solvent, preferably in the presence of sodium methanolate in a mixture of hexane, diethyl ether and/or diisopropyl ether or in the presence of sodium hydride, potassium tert-butylate or a lithium amide in dimethylformamide or dimethyl sulfoxide, with formation of a —CH═CH— bridge or h) an aldehyde of the formula Y—CHO is reacted with a phosphonate of the formula (R$^{VI}$O)$_2$P(O)—CH$_2$—X, in which R$^{VI}$ has the above-stated meaning, under protective gas in the presence of suitable catalysts, preferably sodium methanolate, sodium hydroxide, potassium hydroxide, sodium hydride, potassium tert-butylate or a lithium amide, in a suitable solvent, preferably dimethylformamide, dimethyl sulfoxide, diethyl ether, tetrahydrofuran, with formation of a —CH═CH— bridge and i) optionally the —CH═CH— bridge from step g) or h) is hydrogenated by hydrogen, preferably at standard pressure or elevated pressure of up to 100 bar, in the presence of suitable catalysts, preferably transition metals or transition metal compounds, preferably palladium or the salts thereof, rhodium or the complexes thereof, in a suitable solvent, preferably dimethylformamide, methanol or ethanol, at a temperature of between 20 and 100° C. with formation of a —CH$_2$—CH$_2$ bridge and then worked up and the product is optionally purified, K) optionally the double bond in the 7-membered ring of one of the reaction products from step J) is hydrogenated by hydrogen, preferably at standard pressure or elevated pressure of up to 100 bar, in the presence of suitable catalysts, preferably transition metals or transition metal compounds, preferably palladium or the salts thereof, rhodium or the complexes thereof, in a suitable solvent, preferably dimethylformamide, methanol or ethanol, at a temperature of between 20 and 100° C. and then worked up and the product is optionally purified.

The solvents and reaction conditions used correspond to the solvents and reaction conditions conventional for these types of reactions.

The starting compounds used for the synthesis of the benzo[b]azepin-2-one skeleton, i.e. succinic acid dialkyl esters of the general formula (2) and optionally substituted 2-aminobenzoic acid alkyl esters of the general formula (1), are commercially obtainable.

The reaction of succinic acid dialkyl ester and 2-aminobenzoic acid alkyl esters to yield the precursor of the benzo[b]azepin-2-one is known to the person skilled in the art from the literature as the Schotten-Baumann reaction. The reaction, which leads to ring closure and subsequent conversion to 2,3,4,5-tetrahydrofuryl-1H-benzo[b]azepin-2,5-dione is known from H. B. MacPhillamy et al, Journal of the American Chemical Society, 80, 2172 (1958) and the literature cited therein. The reaction with aminomethylene compounds is known from H. Böhme, K. Hartke, Chemische Berichte, 93, 1305 (1960) and G. Kinast, L.-F, Tietze, Angewandte Chemie, 88, 261 (1976) and the literature cited therein. The reaction with phosphonoalkanoic acid trialkyl esters is described in G. Drefahl, K. Ponsold; H. Schick, Chemische Berichte, 97, 2011 (1964) and the literature cited therein.

Optionally, derivatisation reactions are necessary which introduce the functional groups for linking the benzo[b]azepin-2-one skeleton to the residue X via the bridge A. The saponification of esters proceeds using conventional, methods known to the person skilled in the art. The other reactions are known from the following literature and the literature cited therein: the reduction of carboxylic acids or carboxylic acid esters to yield alcohols O. Vogl, M. Pöhm, Monatsh. Chem. 83, 541 (1952); A. K. Saund, N. K. Mathur; Ind. J. Chem. 9, 936 (1971), The reduction of carboxylic acids or carboxylic acid esters to yield aldehydes A. Ito, R. Takahashi, Y. Baba; Chem, Pharm. Bull, 23, 3081 (1975); E. Winterfeld; Synthesis (1975), 617; H. Khatri, C. H. Stammer; J. Chem. Soc., Chem. Commun. (1979), 79; D. H. Rieh, E. T. O. Sun; J. Med. Chem. 23, 27 (1980), the reaction of alcohols to yield bromides from J. Am Chem. Soc. 48, 1080 (1926); J. Chem. Soc., 636 (1943); Org. Synth. Coll., Vol. 2, 358 (1943); Liebigs Ann. Chem. 626, 26 (1959); J. Am. Chem. Soc, 86, 964 (1964); J. Am. Chem. Soc. 99, 1612 (1977).

The starting compounds for the synthesis of compounds with the residue X$^1$, 1,4-cyclohexanedione monoethylene ketal, 4-oxocyclohexane carboxylic acid and 4-aminocyclohexan-1-one ethylene ketal are known. 1,4-Cyclohexanedione monoethyl ketal and 4-oxocyclohexane carboxylic acid are commercially obtainable or may be obtained using conventional methods known to the person skilled in the art. 4-Aminocyclohexan-1-one ethylene ketal is known from H.-J. Teuber, Liebigs Ann. Chem., 781 (1990) and M. Mimura, Chem. Pharm. Bull., 41, 1971 (1993).

The reactions for synthesising compounds X$^1$—R$^{IV}$ proceed according to conventional methods known to the person skilled in the art. The reaction of a cyclohexanone with a chlorinated or brominated, optionally substituted aromatic or heteroaromatic compound is known from Chem. Ber. 68, 1068 (1935), An. Quim. 64, 607 (1968) and Indian J. Biochem. 5, 79 (1968).

A modification or exchange of the hydroxy group in position 4 of the cyclohexane ring optionally takes place in the residue X$^1$. The reactions may be performed using conventional methods known to the person skilled in the art and are known from the following literature and the literature cited therein: alkylation of the hydroxy group from R. M. Bowman et al, Journal of the Chemical Society (C), 2368 (967); C. G. Neville et al, Journal of the Chemical Society, Perkin Trans, 1, 259 (1991); F. Amt et al, Chemische Berichte, 86, 951 (1953), Journal of Organic Chemistry, 52, 4665 (1987) and Tetrahedron 35, 2169 (1979), arylation or heteroarylation of the hydroxy group from Journal of the American Chemical Society, 107, 3891 (1985), the introduction of a halogen from Journal of the American Chemical Society, 76, 6073 (1954) and Journal of the American Chemical Society, 86, 964 (1964), Journal of the Chemical Society, 636 (1943), Journal of the American Chemical Society, 106, 3286 (1984), Journal of the Chemical Society, 1 2281 (1954) and Synthesis, 746 (1980), the introduction of an alkyl, aryl or heteroaryl residue from A. Suzuki, Acc. Chem. Res., 15,178 (1982); A. Suzuki, Pure Appl. Chem., 57, 1749 (1985); A Suzuki, Pure Appl. Chem., 63, 419 (1991), A. Suzuki, Pure Appl. Chem., 66, 213 (1994), the conversion of chlorides to alkanes from Journal of Organic Chemistry, 23, 1938 (1958), esterification of the hydroxy group from W. König, R. Geiger, Chem. Ber. 103, 788 (1970).

Compounds with residues, which come under the category of general residues $X^2$–$X^{18}$, are known from the following literature: $X^2$ and $X^5$ from German patent application P 3217639, $X^4$ from D. Lednicer, J. Med. Chem., 15, 1235 (1972), $X^3$ and $X^6$ from German patent application P 19525137, $X^7$ and $X^{10}$–$X^{14}$ from E. Friderichs, T. Christoph, H. Buschmann; Analgesics and Antipyretics; in: J. E. Bailey (Ed.); Ullmann's Encyclopedia of Industrial Chemistry, 6th Edition, Wiley-VCH, Weinheim and A. F. Casy, R. T. Parfitt; Opioid Analgesics, Plenum Press, New York, $X^8$ from Forsyth, J. Chem. Soc., 127, 1666 (1925) and P. A. Grieco, J. Org. Chem., 55, 2271 (1990), $X^9$ from Shui, Synth. Commun., 27, 175 (1997), Baisamo, Chim, Ind. (Milan), 58, 519 (1976), Iselin, Helv. Chim. Acta, 37, 178 (1954), $X^{16}$ from German patent applications P 101356366 and P 101356374, $X^{17}$ from S.-H. Zkao, Tetrahedron Letters, 37, 4463 (1996); M. Nishiyama, Tetrahedron Letters, 39, 617 (1998); Jain, J. Med. Chem., 10, 812 (1967), $X^{18}$ from American patent application U.S. Pat. No. 3,041,344 and van de Westeringh, J. Med. Chem., 7, 619 (1964). $X^{15}$ is known as Metamizol in the literature known and is commercially obtainable.

Compounds X—OH, X—NHR$^{1'}$, X—CO(CH$_2$)$_p$OH and X═O are known from the literature or may be produced from known commercially obtainable compounds using conventional, methods known to the person skilled in the art or using methods, such as are described in German patent application P100494811.

Derivatisation reactions are optionally required which introduce the functional groups for linking the residue X with the benzo[b]azepin-2-one skeleton via the bridge A. These reactions may proceed using conventional methods known to the person skilled in the art and are known from the following literature and the literature cited therein: the reaction of ketones to yield aldehydes extended by one carbon are known from German patent application P 100494811; J. Nat. Prod., 44, 557 (1981) and Synth.Commun. 12, 613 (1982), the reduction of aldehydes to alcohols from German patent application P 100494811 and Chem. Commun. 535 (1975), the reaction of alcohols to yield bromides from J. Am Chem. Soc. 48, 1080 (1926); J. Chem. Soc., 636 (1943); Org. Synth. Coll, Vol. 2, 358 (1943); Liebigs Ann, Chem, 626, 26 (1959); J. Am. Chem. Soc. 86, 964 (1964); J. Am. Chem. Soc, 99, 1612 (1977), preparation of phosphonates and phosphonium salts is known from M. Schlosser, Top. Stereochem. 5, 1 (1970); R. Broos, D. Tavernier, M. Anteunis, J. Chem. Educ, 55, 813 (1978); G. Wittig, Angew. Chem. 92, 671 (1980); H. J. Bestmann; Pure Appl. Chem. 52, 771 (1980) and L. Homer, K Hoffmann, H. G. Wippel, G. Klahre; Chem. Ber. 92, 2499 (1959); J. Gillois, G. Guillerm, M. Savignac, E. Stephan, L. Vo Quang, J. Chem. Educ. 57, 161 (1980); B. A. Arbusov; Pure Appl. Chem. 9, 307 (1964); A. K. Bhattacharya, G. Thyagarajan; Chem. Rev. 81, 415 (1981).

Linkage of the residue X with the benzo[b]azepin-2-one skeleton via the bridge A may proceed using conventional methods known to the person skilled in the art and is known from the following literature and the literature in each case cited therein: the reaction of carboxylic acids with alcohols or amines in the presence of dicyclohexylcarbodiimide from W. König, R. Geiger, Chem. Ber. 103, 788 (1970), the reaction of carboxylic acids with alcohols in the presence of 1-(mesitylene-2'-sulfonyl)-3-nitro-1,2,4-triazole from Tetrahedron 36, 3075 (1980), etherification from Tetrahedron 35, 2169 (1979), Tetrahedron Lett. (1973), 21; Synthesis, 434 (1974); J. Org. Chem. 52, 4665 (1987), reductive amination from Org. React 3, 174 (1948); J. Am. Chem. Soc. 91, 3996 (1969); Org. Prep. Proced. Int. 11, 201 (1979); Org. Prep. Proced. Int. 17, 317 (1985), the Wittig or Wittig-Horner-Emmons reaction from G. Wittig, Angew. Chem. 92, 671 (1980); H. J. Bestmann; Pure Appl. Chem. 52, 771 (1980) and L. Horner, H. Hoffmann, H. G. Wippel, G. Klahre; Chem. Ber., 92, 2499 (1959); J. Gillois, G. Guillerm, M. Savignac, E. Stephan, L. Vo Quang; J. Chem. Educ. 57, 161 (1980); B. A. Arbusov; Pure Appl. Chem. 9, 307 (1964); A. K. Bhattacharya, G. Thyagarajan; Chem. Rev. 81, 415 (1981) and hydrogenation from Synthesis (1978), 329; J. Org. Chem. 34, 3684 (1969); J. Am. Chem. Soc. 91, 2579 (1969).

The corresponding literature descriptions are hereby introduced as a reference and are deemed to be part of the disclosure.

The substituted benzo[b]azepin-2-one compounds according to the invention of the general formulae I and II and in each case the tautomers and corresponding stereoisomers thereof may be isolated both in the form of the free bases thereof and in the form of corresponding salts.

The free bases of the respective compounds according to the invention of the general formulae I and II, the tautomers and corresponding stereoisomers thereof may be converted into the corresponding physiologically acceptable salts by reaction with an inorganic or organic acid, preferably with hydrochloric acid, hydrobromic acid, sulfuric acid, phosphoric acid, methanesulfonic acid, p-toluenesulfonic acid, carbonic acid, formic acid, acetic acid, oxalic acid, succinic acid, tartaric acid, mandelic acid, fumaric acid, lactic acid, citric acid, glutamic acid or aspartic acid. The free bases of the respective compounds according to the invention of the general formulae I or II, the tautomers and corresponding stereoisomers thereof may likewise preferably be converted into the corresponding hydrochlorides by combining the compounds according to the invention of the general formulae I or II dissolved in a suitable organic solvent, such as for example butane-2-one (methyl ethyl ketone), the tautomers and corresponding stereoisomers thereof as free bases with trimethylsilyl chloride (TMSCl).

The free bases of the respective compounds according to the invention of the general formulae I or II, the tautomers and corresponding stereoisomers thereof may be converted into the corresponding physiologically acceptable salts with the free acid or a salt of a sugar substitute, such as for example saccharin, cyclamate or acesulfame.

The compounds according to the invention of the general formulae I and II, the tautomers and in each case corresponding stereoisomers thereof may optionally, like the corresponding acids, the corresponding bases or salts of these compounds, also be obtained in the form of the solvates thereof, preferably the hydrates thereof.

If the substituted benzo[b]azepin-2-one compounds according to the invention of the general formulae I and II and the tautomers thereof are obtained by the production process according to the invention in the form of stereoisomers, preferably in the form of the racemates thereof or other mixtures of their various enantiomers and/or diastereomers, these may be separated and optionally isolated by conventional processes known to the person skilled in the art. Examples are chromatographic separation processes, in particular liquid chromatography processes at standard pressure or at elevated pressure, preferably MPLC and HPLC processes, and fractional crystallisation processes. Individual enantiomers, e.g. diastereomeric salts formed by means of HPLC on a chiral phase or by means of crystallisation with chiral acids, such as (+)-tartaric acid, (−)-tartaric acid or (+)-10-camphorsulfonic acid, may here in particular be separated from one another.

The substituted benzo[b]azepin-2-one compounds according to the invention of the general formulae I and II, the tautomers and corresponding stereoisomers thereof as well as in each case the corresponding bases, salts and solvates are toxicologically safe and are therefore suitable as pharmaceutical active ingredients in pharmaceutical preparations.

The present invention accordingly further provides pharmaceutical preparations, which contain at least one substituted benzo[b]azepin-2-one compound according to the invention of the general formulae I or II and/or a corresponding tautomer, optionally in the form of the racemate thereof, the pure stereoisomer thereof, in particular enantiomer or diastereomer, or in the form of mixtures of the stereoisomers, in particular the enantiomers or diastereomers, in any desired mixing ratio or in each case in the form of the acid or bases thereof or in the form of the salt thereof, in particular the physiologically acceptable salt, or in the form of the solvate thereof, in particular the hydrate, optionally together with physiologically acceptable auxiliary substances. It goes without saying that the pharmaceutical preparations according to the invention may also comprise mixtures of two or more of the above-stated compounds according to the invention.

If the substituted benzo[b]azepin-2-one compounds according to the invention of the general formulae I and II or the tautomers thereof or the corresponding salts, bases or solvates thereof are chiral, they may, as stated above, be present in the pharmaceutical preparation according to the invention in the form of the racemates thereof, the pure enantiomers thereof, the pure diastereomers thereof or in the form of a mixture of at least two of the above-mentioned stereoisomers.

The pharmaceutical preparations according to the invention are preferably suitable for the combatting of pain, preferably of chronic or neuropathic pain, and for the treatment or prevention of neurodegenerative diseases, preferably Alzheimer's disease, Huntington's chorea or Parkinson's disease, stroke, cerebral infarct, cerebral ischaemia, cerebral oedema, insufficiency states of the central nervous system, preferably hypoxia or anoxia, epilepsy, schizophrenia, psychoses brought about by elevated amino acid levels, AIDS dementia, encephalomyelitis, Tourette's syndrome, perinatal asphyxia, tinnitus, migraine, inflammatory and/or allergic reactions, depression, mental health conditions, urinary incontinence, pruritus or diarrhoea or for anxiolysis or anaesthesia.

The present invention also provides the use of at least one substituted benzo[b]azepin-2-one compound of the general formulae I or II or a tautomer, optionally in the form of the racemate thereof, the pure stereoisomer thereof, in particular enantiomer or diastereomer, or in the form of mixtures of the stereoisomers, in particular the enantiomers or diastereomers, in any desired mixing ratio or in each case in the form of the acid or base thereof or in the form of the salt thereof, in particular a physiologically acceptable salt, or in the form of the solvate thereof, in particular the hydrate, for the production of a pharmaceutical preparation for the combatting of pain, preferably of chronic or neuropathic pain, and for the treatment or prevention of neurodegenerative diseases, preferably Alzheimer's disease, Huntington's chorea or Parkinson's disease, stroke, cerebral infarct, cerebral ischaemia, cerebral oedema, insufficiency states of the central nervous system, preferably hypoxia or anoxia, epilepsy, schizophrenia, psychoses brought about by elevated amino acid levels, AIDS dementia, encephalomyelitis, Tourette's syndrome, perinatal asphyxia, tinnitus, migraine, inflammatory and/or allergic reactions, depression, mental health conditions, urinary incontinence, pruritus or diarrhoea or for anxiolysis or anaesthesia.

The pharmaceutical preparations according to the invention may be present as liquid, semisolid or solid dosage forms, for example in the form of solutions for injection, drops, succi, syrups, sprays, suspensions, tablets, patches, capsules, transdermal delivery systems, suppositories, ointments, creams, lotions, gels, emulsions, aerosols or in multiparticulate form, for example in the form of pellets or granules, and also be administered as such.

In addition to at least one substituted benzo[b]azepin-2-one compound according to the invention of the general formulae I or II and/or a corresponding tautomer, optionally in the form of the racemate thereof, the pure stereoisomer thereof, in particular enantiomer or diastereomer, or in the form of mixtures of the stereoisomers, in particular the enantiomers or diastereomers, in any desired mixing ratio or in each case in the form of the acid or base thereof or in the form of the salt thereof, in particular a physiologically acceptable salt, or in the form of the solvate thereof, in particular the hydrate, the pharmaceutical preparations according to the invention conventionally contain further physiologically acceptable pharmaceutical auxiliary substances, which are preferably selected from the group consisting of matrix materials, fillers, solvents, diluents, surface-active substances, dyes, preservatives, suspending agents, slip agents, lubricants, aromas and binders.

Selection of the physiologically acceptable auxiliary substances and the quantities thereof which are to be used depends upon whether the pharmaceutical preparation is to be administered orally, subcutaneously, parenterally, intravenously, intraperitoneally, intradermally, intramuscularly, intranasally, buccally, rectally or topically, for example onto infections of the skin, mucous membranes or eyes. Preparations in the form of tablets, coated tablets, capsules, granules, pellets, drops, succi and syrups are preferred for oral administration, while solutions, suspensions, readily reconstitutible dried preparations and sprays are preferred for parenteral, topical and inhalatory administration. Compounds according to the invention of the general formulae I or II or the tautomers thereof, optionally in the form of the racemates thereof, the pure stereoisomers thereof, in particular enantiomers or diastereomers, or in the form of mixtures of the stereoisomers, in particular the enantiomers or diastereomers, in any desired mixing ratio or in each case in the form of the acids or bases thereof or in the form of the salts thereof, in particular physiologically acceptable salts, or in the form of the solvates thereof, in particular hydrates, in a depot in dissolved form or in a dressing, optionally with the addition of skin penetration promoters, are suitable percutaneous administration preparations. Orally or percutaneously administrable formulations may also release the compounds according to the invention in delayed manner.

Production of the pharmaceutical preparations according to the invention proceeds with the assistance of conventional means, devices, methods and processes known to the person skilled in the art, such as are described for example in "Remington's Pharmaceutical Sciences", ed. A. R. Gennaro, 17th ed., Mack Publishing Company, Easton, Pa. (1985), in particular in part 8, chapters 76 to 93. The corresponding literature description is hereby introduced as a reference and is deemed to be part of the disclosure.

The quantity to be administered to the patient of the respective substituted benzo[b]azepin-2-one compound according to the invention of the general formulae I or II or of a tautomer thereof, optionally in the form of the racemate thereof, the pure stereoisomer thereof, in particular enantiomer or diastereomer, or in the form of mixtures of the stereoisomers, in particular the enantiomers or diastereomers, in any desired mixing ratio or in each case in the form of the acid or base thereof or in the form of the salt thereof, in particular a physiologically acceptable salt, or in the form of the solvate thereof, in particular the hydrate, may vary and is for example dependent on the weight or age of the patient and on the mode of administration, the indication and the severity of the complaint. Conventionally, at least one compound according to the invention is administered in a quantity of 0.005 to 500 mg/kg, preferably of 0.05 to 5 mg/kg, of patient body weight.

The investigation into analgesic efficacy was performed by phenylquinone-induced writhing in mice (modified after: I. C. Hendershot, J. Forsaith, J. Pharmacol. Exp. There. 125, 237–240 (1959)). The corresponding literature description is hereby introduced as a reference and is deemed to be part of the disclosure.

Male NMRI mice weighing from 25 to 30 g were used for this purpose. Groups of 10 animals per substance dose received, 10 minutes after intravenous administration of the compounds tested, 0.3 ml/mouse of a 0.02% aqueous solution of phenylquinone (phenylbenzoquinone, Sigma, Deisenhofen; solution prepared with addition of 5% of ethanol and stored in a water bath at 45° C.) administered intraperitoneally. The animals were placed individually in observation cages. A push button counter was used to record the number of pain-induced stretching movements (writhing reactions=straightening of the torso with stretching of the rear extremities) for 5–20 minutes after phenylquinone administration. The control was provided by animals who received only physiological common salt solution.

The compounds were tested at the standard dosage of 10 mg/kg. Inhibition of the writhing reactions by a substance was calculated according to the following formula:

$$\% \text{ Inhibition} = 100 - \left[ \frac{\text{Writhing reaction, treated animals}}{\text{Writhing reaction, control}} \times 100 \right]$$

DETAILED DESCRIPTION OF THE PREFERRED EMBODIMENT(S)

The invention is explained below with reference to Examples. These explanations are given merely by way of example and do not restrict the general concept of the invention.

EXAMPLES

The yields of the example compounds according to the invention were not optimised.

Example 1

Synthesis of 2'-(8-chloro-2-oxo-2,3-dihydro-1H-benzo[b]azepin-5-yl) acetic acid

1st step:

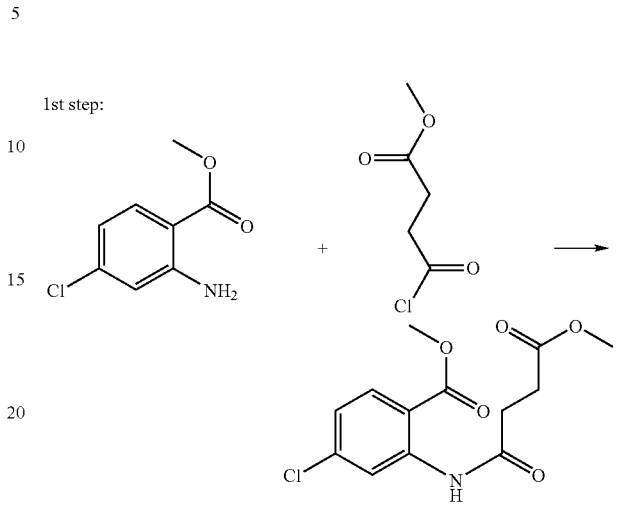

N-acylation of 2-amino-4-chlorobenzoic acid methyl ester with succinic acid methyl ester chloride in pyridine yielded N-(2-carbomethoxy-5-chlorophenyl) succinic acid methyl ester amide with a yield of 90%. The melting point of the compound was 95–96° C.

2nd step:

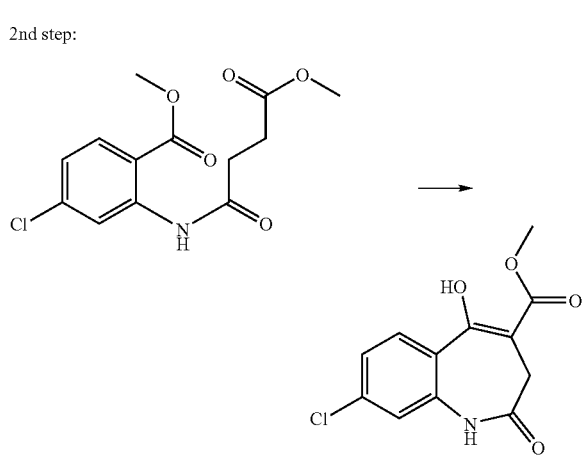

40 g (133 mmol) of N-(2-carbomethoxy-5-chlorophenyl) succinic acid methyl ester were reacted in THF in the presence of potassium tert-butanolate for 5 hours at room temperature to yield 8-chloro-5-hydroxy-2-oxo-2,3-dihydro-1H-benzo[b]azepin-4-carboxylic acid methyl ester. The yield was 81%.

3rd step:

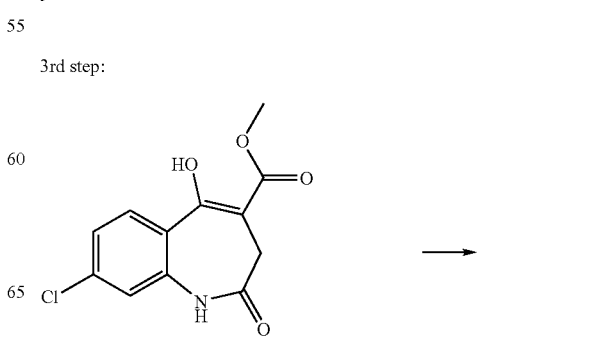

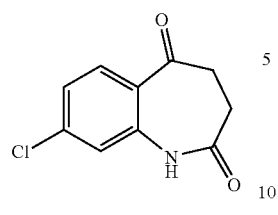

30.0 g (0.11 mol) of 8-chloro-5-hydroxy-2-oxo-2,3-dihydro-1H-benzo[b]azepin-4-carboxylic acid methyl ester were heated in DMSO/H$_2$O (9:1) to 150° C. for 6 hours. The yield of 8-chloro-2,3,4,5-tetrahydro-1H-benzo[b]azepin-2,5-dione amounted to 83%.

4th step:

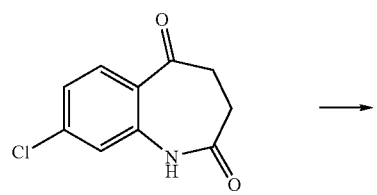

6.0 g (28.6 mmol) of 8-chloro-2,3,4,5-tetrahydro-1H-benzo[b]azepin-2,5-dione were reacted with 7.7 (34.3 mmol) of phosphonoacetic acid triethyl ester and 3.85 (34.34 mmol) of potassium tert-butanolate in DMF for 8 hours at 65° C. under argon. 2'-(8-Chloro-2-oxo-2,3-dihydro-1H-benzo[b]azepin-5-yl) acetic acid ethyl ester was obtained as a yellow oil with a yield of 4.23 g (53%).

5th step:

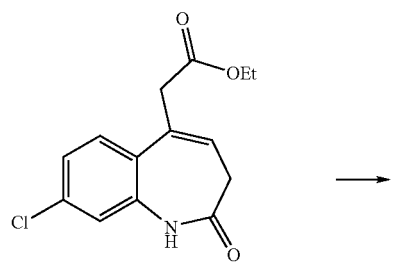

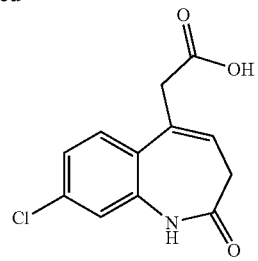

4.23 g (15 mmol) of 2'-(8-chloro-2-oxo-2,3-dihydro-1H-benzo[b]azepin-5-yl) acetic acid ethyl ester was saponified with 5% aqueous KOH for 4 hours at room temperature. After acidification of the solution, 2'-(8-chloro-2-oxo-2,3-dihydro-1H-benzo[b]azepin-5-yl) acetic acid precipitated as a light yellow precipitate. The precipitate was separated, washed with water and diethyl ether and dried. The yield was 2.27 mg (60%).

Example 2

Synthesis of 2'-(8-chloro-1-methyl-2-oxo-2,3-dihydro-1H-benzo[b]azepin-5-yl) acetic acid Preparation of the compound proceeded in a manner similar to Example 1 with 2-(N-methylamino)-4-chlorobenzoic acid methyl ester as educt.

Example 3

Synthesis of 8-chloro-4-(N,N-dimethylaminomethyl)-2,3,4,5-tetrahydro-1H-benzo[b]azepin-2,5-dione hydrochloride

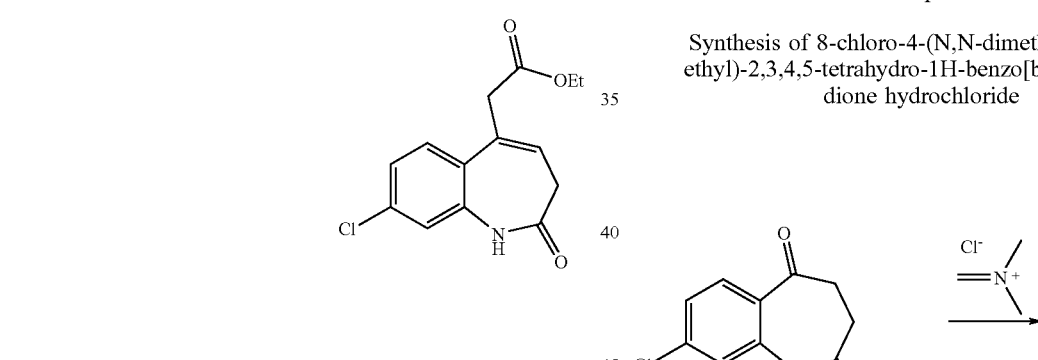

8-Chloro-2,3,4,5-tetrahydro-1H-benzo[b]azepin-2,5-dione was reacted with N,N-dimethylaminomethylene hydrochloride in acetonitrile with acid catalysis with acetyl chloride for 5 hours at 20° C. The yield of 8-chloro-4-(N,N-dimethylaminomethyl)-2,3,4,5-tetrahydro-1H-benzo[b]azepin-2,5-dione hydrochloride was 85%. The compound was obtained as a yellow, fine crystalline substance.

Example 4

Synthesis of 2'-(8-chloro-1-methyl-2-oxo-2,3-dihydro-1H-benzo[b]azepin-5-yl) acetic acid [3"-(N,N-dimethylaminomethyl)-4"-hydroxy-4"-(m-methoxyphenyl)cyclohexyl]ester 95:5). The product was obtained as a colourless substance with a yield of 378 mg (54%).

Example 5

Synthesis of 2'-(8-chloro-2-oxo-2,3-dihydro-1H-benzo[b]azepin-5-yl) acetic acid [3"-(N,N-dimethylaminomethyl)-4"-hydroxy-4"-(m-methoxyphenyl)cyclohexyl]ester

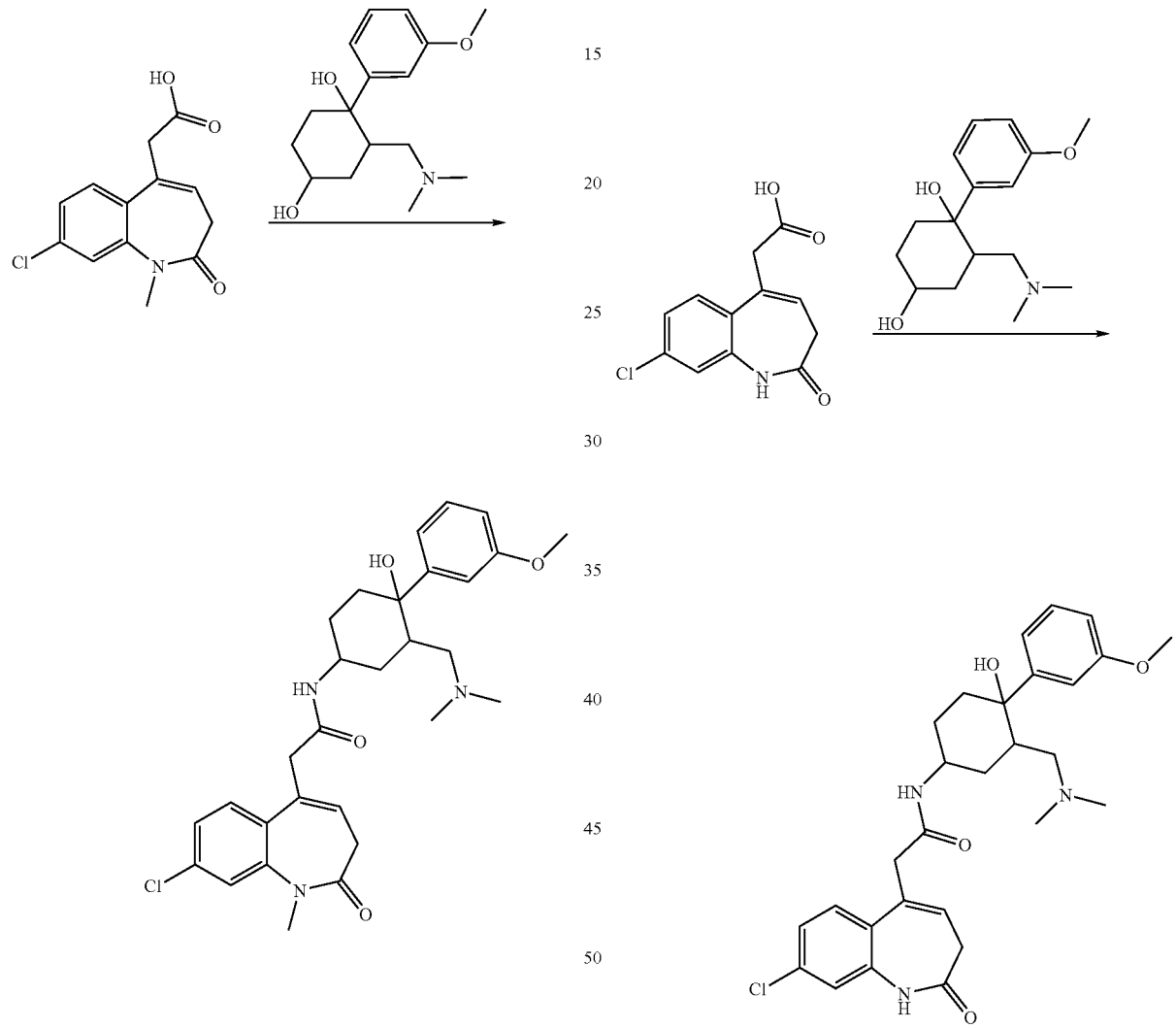

2'-(8-Chloro-1-methyl-2-oxo-2,3-dihydro-1H-benzo[b]azepin-5-yl)-O-([3"-(N,N-dimethylaminomethyl)-4"-hydroxy-4"-(m-methoxyphenyl)cyclohexyl] acetate was obtained by esterification of 352 mg (1.32 mmol) of 2'-(8-chloro-1-methyl-2-oxo-2,3-dihydro-1H-benzo[b]azepin-5-yl) acetic acid with 370 mg (1.32 mmol) of 2-(N,N-dimethylaminomethyl)-1-(m-methoxyphenyl)cyclohexane-1,4-diol in the presence of 82 mg (1.0 mmol) of 1-methylimidazole and 340 mg (1.32 mmol) 1-(mesitylene-2'-sulfonyl)-3-nitro-1,2,4-triazole in methylene chloride for 48 hours at 20° C. The reaction product was purified by means of column chromatography (chloroform/methanol, 2'-(8-Chloro-2-oxo-2,3-dihydro-1H-benzo[b]azepin-5-yl)-O-[3"-(N,N-dimethylaminomethyl)-4"-hydroxy-4"-(m-methoxyphenyl)cyclohexyl]acetate was prepared in a manner similar to Example 4 from 2-(N,N-dimethylaminomethyl)-1-(m-methoxyphenyl)cyclohexane-1,4-diol and 2'-(8-chloro-2-oxo-2,3-dihydro-1H-benzo[b]azepin-5-yl) acetic acid. The yield was 503 mg (65%). The compound had a melting point of 105–110° C.

Example 6

Synthesis of 2'-(8-chloro-1-methyl-2-oxo-2,3-dihydro-1H-benzo[b]azepin-5-yl)-N-[3"-(N,N-dimethylaminomethyl)-4"-hydroxy-4"-(m-methoxyphenyl)cyclohexyl]acetamide

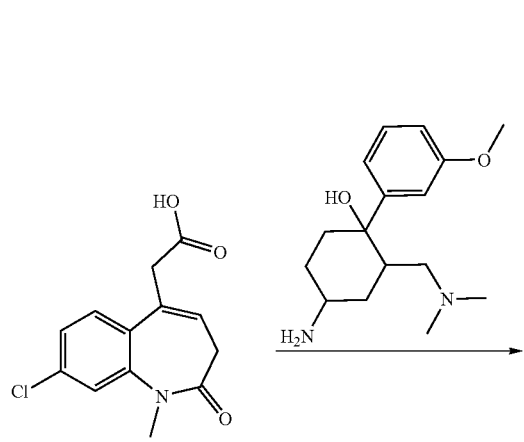

314 mg (1.13 mmol) of 4-amino-2-(N,N-dimethylaminomethyl)-1-(m-methoxyphenyl)-cyclohexan-1-ol and 300 mg (1.13 mmol) of 2'-(8-chloro-1-methyl-2-oxo-2,3-dihydro-1H-benzo[b]azepin-5-yl) acetic acid were reacted in 15 ml of DMF in the presence of 443 mg (2.14 mmol) of dicyclohexylcarbodiimide, 217 ml (2.14 mmol) of N-methylmorpholine and 290 mg (2.14 mmol) of 1-hydroxybenzotriazole to yield the amide. The product was purified using column chromatography (ethyl acetate/methanol/acetic acid, 60:38:2). The yield was 443 mg (75%).

Example 7

Synthesis of 2'-(8-chloro-2-oxo-2,3-dihydro-1H-benzo[b]azepin-5-yl)-N-[3"-(N,N-dimethylaminomethyl)-4"-hydroxy-4"-(m-methoxyphenyl)cyclohexyl]acetamide

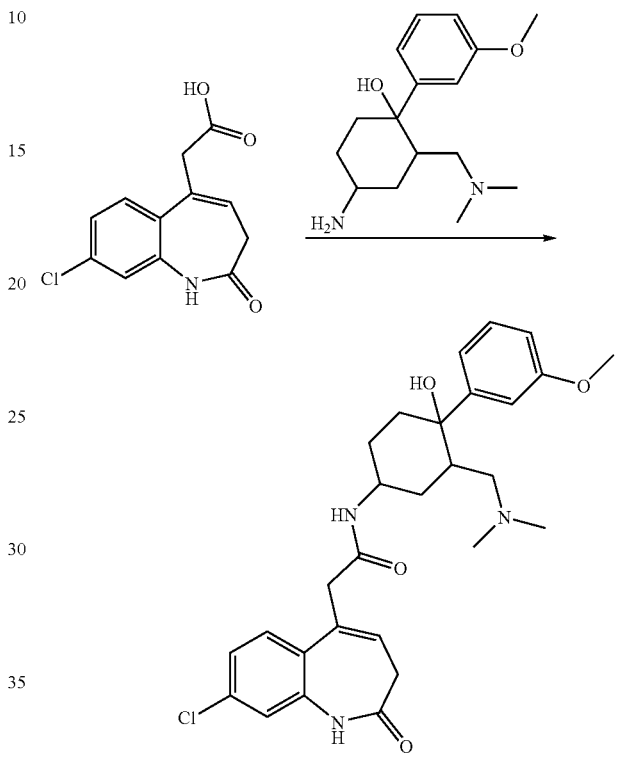

2'-(8-Chloro-2-oxo-2,3-dihydro-1H-benzo[b]azepin-5-yl)-N-[3"-(N,N-dimethylaminomethyl)-4"-hydroxy-4"-(m-methoxyphenyl)cyclohexyl]acetamide was produced in a manner similar to Example 6 from 4-amino-2-(N,N-dimethylaminomethyl)-1-(m-methoxyphenyl)cyclohexan-1-ol and 2'-(8-chloro-2-oxo-2,3-dihydro-1H-benzo[b]azepin-5-yl) acetic acid. The yield was 40%. The amide had a melting point of 205–210° C.

Pharmacological Investigations

Analgesic Testing by Writhing Test in Mice:

The in-depth investigation into analgesic efficacy was performed using phenylquinone-induced writhing in mice, as described above.

The investigated compounds according to the invention exhibited an analgesic action. The results of selected writhing investigations are summarised in Table 1 below.

TABLE 1

| Example no. | % inhibition of writhing reactions 10 mg/kg i.v. |
|---|---|
| 4 | 39 |
| 5 | 63 |
| 6 | 25 |

What is claimed is:

1. A compound of formulae I or II,

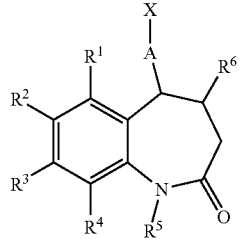

I

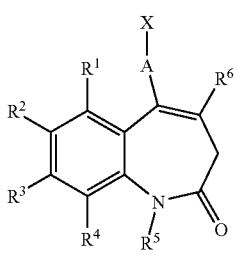

II in which
R¹, R², R³ and R⁴, identical or different, denote a linear or branched, saturated or unsaturated aliphatic $C_{1-10}$ group or a saturated or unsaturated cycloaliphatic $C_{3-7}$ group, wherein each of the above-stated groups may optionally be bonded via an ether bridge, or hydrogen, a halogen or a hydroxy group, R⁵ denotes hydrogen, a linear or branched, saturated or unsaturated aliphatic $C_{-10}$ group, or an aryl group, R⁶ denotes hydrogen or a group of the formula —CH₂—NR⁷₂, wherein the two groups R⁷ are identical or different and have the meaning stated below or may form a 3–8-membered ring together with the nitrogen atom connecting them as a ring member, R⁷ denotes a linear or branched, saturated or unsaturated aliphatic $C_{1-6}$ group or a saturated or unsaturated cycloaliphatic $C_{3-6}$ group, A denotes a bridge with one of the following formulae: —(CH₂)$_{n+2}$—, —(CH₂)$_n$—CH=CH—, —(CH₂)$_n$COO—, —(CH₂)$_n$CONH—, —(CH₂)n+1 (CH₂)$_p$ CO—, —(CH₂)$_{n+1}$O—, —(CH₂)$_{n+1}$NR¹'— in which n denotes 0, 1, 2, or 3, and p denotes 0 or 1, R¹' has the meaning stated hereinafter and the bond to the group X is always stated last, and X denotes one of the following groups of the general formulae X¹ to X⁶ and X¹⁶, in which the unoccupied bond line symbolises the bond to the bridge A and

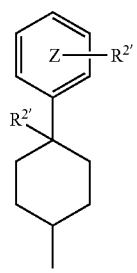
X¹

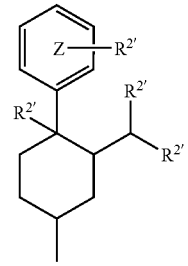
X²

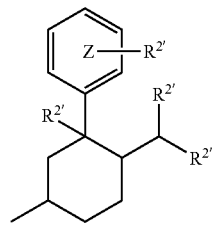
X³

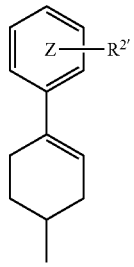
X⁴

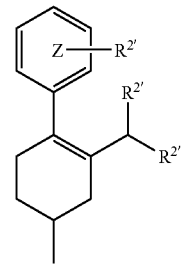
X⁵

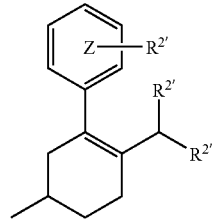
X⁶

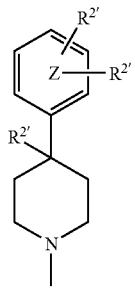
X⁷

-continued

X⁸ 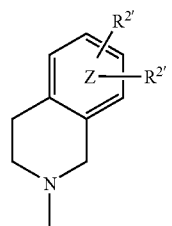

X⁹ 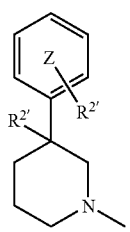

X¹⁰ 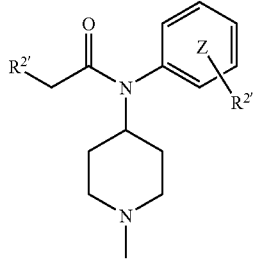

X¹¹ 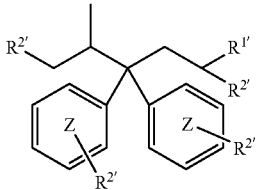

X¹² 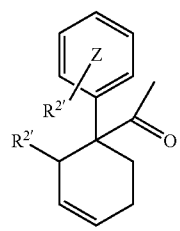

X¹³ 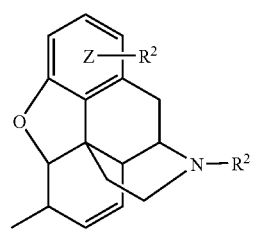

-continued

X¹⁴ 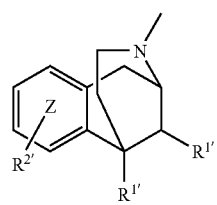

X¹⁵ 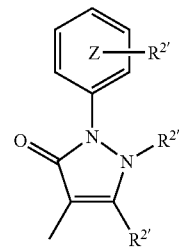

X¹⁶ 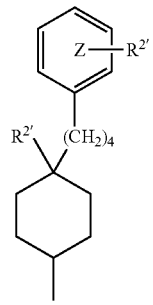

X¹⁷ 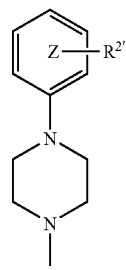

X¹⁸ 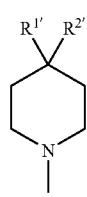

in which $R^{1'}$ denotes hydrogen, a linear or branched, saturated or unsaturated aliphatic $C_{1-10}$ group, a saturated or unsaturated cycloaliphatic $C_{3-7}$ group, or an aryl group, $R^{2'}$ denotes a linear or branched, saturated or unsaturated aliphatic $C_{1-10}$ group, a saturated or unsaturated cycloaliphatic $C_{3-7}$ group or an aryl group wherein all above-stated groups may optionally be joined via an ether, thioether or SO$_2$ bridge, or hydrogen, a halogen, a hydroxy, thiol, cyano or nitro group or a group of the formula —NR1'$_2$ wherein the two groups R$^{1'}$ are identical or different and have the above-stated meaning, R$^{3'}$ denotes a lineart or branched, saturated or unsaturated aliphatiC C$_{1-10}$ group, a saturated or unsaturated cycloaliphatic C$_{3-7}$ group, or an aryl group, wherein all the above-stated group may optionally be joined via an ether or an ester bridge, hydrogen, a halogen, a hydroxy group, R$^{4'}$ denotes hydrogen, or an aryl group, wherein the aryl group may comprise at least one substituent R$^{2'}$ with the above meaning, with the exception of hydrogen, R$^{5'}$ denotes a of the formula -NR$^{6'}_2$, wherein the two R$^{6'}$ may be identical or different and have the meaning stated hereinafter or may form a 3–7-membered ring together with the nitrogen atom connecting them as a ring member, which ring may optionally contain at least one oxygen and/or at least one further nitrogen as a ring atom, wherein the nitrogen may comprise a substituent R$^{10'}$ with the meaning stated hereinafter, R$^{6'}$ denotes a linear or branched, saturated or unsaturated aliphatic C$_{1-6}$ group, a saturated or unsaturated cycloaliphatic C$_{3-7}$ group, or an aryl group, R$^{9'}$ denotes hydrogen, a linear or branched aliphatic C$_{1-10}$ residue, R$^{10'}$ denotes hydrogen, a linear or branched, saturated or unsaturated aliphatic C$_{1-10}$ group, or an aryl group and Z denotes at least one optionally present nitrogen as a ring atom, and q denotes 0, 1, 2 or 3, optionally in the form of the racemates thereof, the pure stereoisomers thereof, or in the form of mixtures of the stereoisomers, in any desired mixing ratio or in each case in the form of the acids or bases thereof or in the form of the salts thereof.

2. A compound according to claim 1, characterised in that R$^2$ and R$^3$, identical or different, denote a linear or branched, saturated or unsaturated aliphatic C$_{1-3}$ group or a halogen and R$^1$ and R$^4$ in each case denote hydrogen, R$^5$ denotes hydrogen or a linear or branched, saturated or unsaturated aliphatic C$_{1-3}$ group and R$^6$ denotes hydrogen or a group of the formula —CH$_2$—NR$^7_2$, in which R$^7$ denotes a linear or branched, saturated or unsaturated aliphatic C$_{1-3}$ group, optionally in the form of the racemates thereof, the pure stereolsomers thereof, enantiomers or diastereomers, or in the form of mixtures of the stereoisomers, in any desired mixing ratio or in each case in the form of the acids or bases thereof or in the form of the salts thereof.

3. Substituted benzo[b]azepin2-one compounds and in each case the tautomers thereof A compound according to claim 1, characterised in that R2 and R3 in each case denote a methyl group or a chlorine and R1 and R4 in each case denote hydrogen, R5 denotes hydrogen or a methyl group and R6 denotes hydrogen or a group residue of the formula —CH$_2$—N(CH$_3$)$_2$, optionally in the form of the racemates thereof, the pure stersoisomers thereof or in the form of mixtures of the stereoisomers, in any desired mixing ratio or in each case in the form of the acids or bases thereof or in the form of the salts thereof.

4. A compound according to claim 1, characterized in that R$^3$ denotes a linear or branched, saturated or unsaturated aliphatic C$_{1-3}$ group or a halogen and R$^1$, R$^2$ and R$^4$ in each case denote hydrogen, R$^5$ denotes hydrogen or a linear or branched, saturated or unsaturated aliphatic C$_{1-3}$ group and R$^6$ denotes hydrogen or a group of the formula —CH$_2$—N (R$^7$)$_2$, in which R$^7$ denotes a linear or branched, saturated or unsaturated aliphatic C$_{1-3}$ group, optionally in the form of the racemates thereof, the pure stereoisomers thereof or in the form of mixtures of the stereoisomers, in any desired mixing ratio or in each case in the form of the acids or bases thereof or in the form of the salts thereof.

5. A compound according to claim 1, characterised in that R$^3$ denotes a methyl group or a chlorine and R$^1$, R$^2$ and R$^4$ in each case denote hydrogen, R$^5$ denotes hydrogen or a methyl group and R$^6$ denotes hydrogen or a of the formula —CH$_2$—N(CH$_3$)$_2$, optionally in the form of the racemates thereof, the pure stereoisomers thereof, or in the form of mixtures of the stereoisomers, in any desired mixing ratio or in each case in the form of the acids or bases thereof or in the form of the salts thereof.

6. A compound according to claim 1, characterised in that R$^1$ and R$^3$, identical or different, denote a linear or branched, saturated or unsaturated aliphatic c$_{1-3}$ group or a halogen and R$^2$ and R$^4$ in each case denote hydrogen, R$^5$ denotes hydrogen or a linear or branched, saturated or unsaturated aliphatic C$_{1-3}$ group and R$^6$ denotes hydrogen or a group of the formula —CH$_2$—NR$^7_2$, in which R$^7$ denotes a linear or branched, saturated or is unsaturated aliphatic c$_{1-3}$ group, optionally in the form of the racemates thereof, the pure stereoisomers thereof, or in the form of mixtures of the stereoisomers, in any desired mixing ratio or in each case in the form of the acids or bases thereof or in the form of the salts thereof.

7. A compound according to claim 1, characterised in that R$^1$ and R$^3$ in each case denote a methyl group or a chlorine and R$^2$ and R$^4$ in each case denote hydrogen, R$^5$ denotes hydrogen or a methyl group and R$^6$ denotes hydrogen or a of the formula —CH$_2$—N(CH$_3$)$_2$, optionally in the form of the racemates thereof, the pure stereoisomers thereof, or in the form of mixtures of the stereoisomers, in any desired mixing ratio or in each case in the form of the acids or bases thereof or in the form of the salts thereof.

8. A compound according to claim 1, characterised in that A denotes a bridge of the formula —CH$_2$—COO— or —CH$_2$CONH— optionally in form of the racemates thereof, the pure stereoisomers thereof, in particular enantiomers or diastereomers, or in the form of mixtures of the stereoisomers, in any desired mixing ratio or in each case in the form of the acids or bases thereof or in the form of the salts thereof.

9. A compound according to claim 1, characterised in that X denotes a group of the following formula:

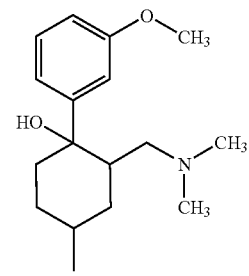

optionally in the form of the racemates thereof, the pure stereoisomers thereof or in the form of mixtures of the stereoisomers, in any desired mixing ratio or in each case in the form of the acids or bases thereof or in the form of the salts thereof.

10. A compound according to claim 1 which is:
2'-(8-Chloro-2-oxo-2,3-dihydro-1H-benzo[b]azepin-5-yl) acetic acid [3"-(N,N-dimethylaminomethyl)-4"-hydroxy-4"-(m-methoxyphenyl)cyclohexyl]ester,
2'-(8-Chloro-1-methyl-2-oxo-2,3-dihydro-1H-benzo[b]azepin-5-yl) acetic acid [3"-(N,N-dimethylaminomethyl)-4"-hydroxy-4"-(m-methoxyphenyl)cyclohexyl]ester,
2'-(8-Chloro-2-oxo-2,3-dihydro-1H-benzo[b]azepin-5-yl)-N-[3"-N,N-dimethylaminomethyl)-4"-hydroxy-4"-(m-methoxyphenyl)cyclohexyl]acetamide,
2'-(8-Chloro-1methyl-2-oxo-2,3-dihydro-1H-benzo[b]azepin-5-yl)-N-[3"-(N,N-dimethylaminomethyl)-4"-hydroxy-4"-(m-methoxyphenyl)cyclohexyl]acetamide,
optionally in the form of the racemates thereof, the pure stersoisomers thereof, or in the form of mixtures of the stereoisomers, in any desired mixing ratio or in each case in the form of the acids or bases thereof or in the form of the salts thereof.

11. A process for the production of a compound according to claim 1, characterised in that
A) an optionally substituted 2-aminobenzoic alkyl ester of the formula (1), in which $R^1$, $R^2$, $R^3$, $R^4$ and $R^5$ have the same meaning as in claim 1 and R denotes an alkyl group,

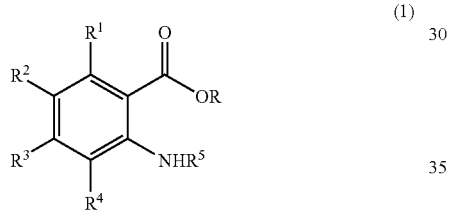

is reacted with succinic acid dialkyl ester of the formula (2), in which R' denotes an alkyl group and $R^x$ denotes chlorine or an alkoxy group,

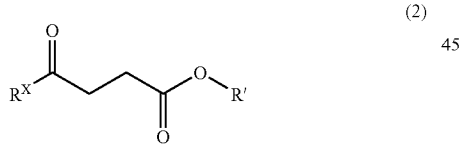

under suitable reaction conditions, in a suitable solvent, and is then worked up, optionally followed by purification of the optionally substituted N-(2-carbalkoxyphenyl)succinic acid alkyl ester amide formed of the formula (3), in which R, R', $R^1$ $R^2$, $R^3$, $R^4$ and $R^5$ have the above-stated meaning

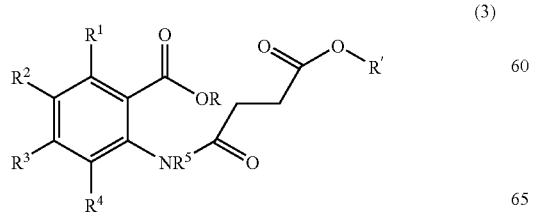

B) an optionally substituted N-(2-carboalkoxyphenyl) succinic acid alkyl ester amide of the formula (3) is reacted in the presence of potassium tert-butanolate in a suitable solvent and

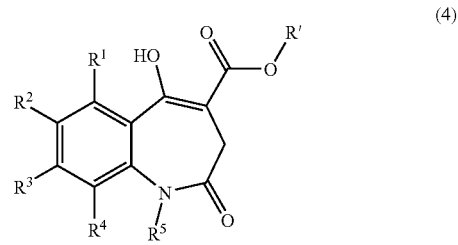

then worked up, optionally followed by purification of the optionally substituted 5-hydroxy-2-oxo-2,3-dihydro-1H-benzo[b]azepin-4-carboxlic acid alkyl ester formed of the general formula (4), in which R', $R^1$, $R^2$, $R^3$, $R^4$ and $R^5$ have the above-stated meaning, C) an optionally substituted 5-hydroxy-2-oxo-2,3-dihydro-1H-benzo[b]azepin-4-carboxylic acid alkyl ester of the general formula (4) is reacted in a dimethyl sulfoxide/Water mixture at elevated temperature and then worked up, optionally followed by purification of the optionally substituted 2,3,4,5-tetrahydro-1H-benzo[b]azepin-2,5-dione of the general formula (5), in which R', $R^2$, $R^3$ $R^4$ and $^5$ have the above-stated meaning,

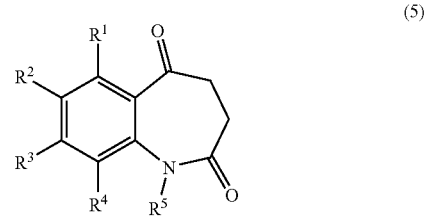

D) an optionally substituted 2,3,4,5-tetrahydro-1H-benzo[b]azepin-2,5-done of the formula (5) is reacted with a substituted aminomethyl hydrochloride of the formula (6), in which the group $R^7$ has the meaning stated in claim 1,

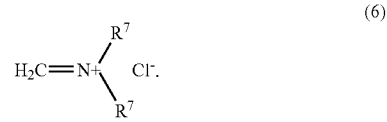

in the presence of an acid, in a suitable solvent, and then worked up, optionally followed by purification of the optionally substituted aminomethyl-2,3,4,5-tetrahydro-1H-benzo[b]-azepin-2,5-dione of the formula (7), in which $R^1$, $R^2$, $R^3$, $R^4$, $R^5$ and $R^7$ have the above-stated meaning,

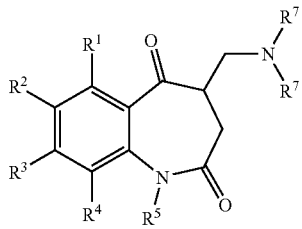

E) an optionally substituted 2,3,4,5-tetrahydro-1H-benzo[b]azepin-2,5-dione of the formula (8), in which R', $R^2$, $R^3$, $R^4$, $R^5$ and $R^6$ have the same meaning as in claim 1 and which combines the compounds of the formulae (5) and (7)

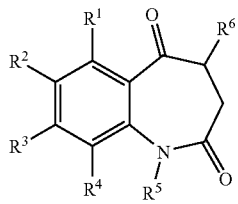

is reacted with a phosphonoalkanoic acid trialkyl ester of the formula (9), in which n has the same meaning as in claim 1 and R" denotes an alkyl group,

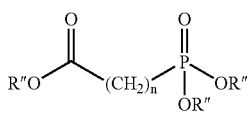

in the presence of a base, in a suitable solvent, and then worked up, optionally followed by Purification of the compound formed of the formula Y—COOR" in which R" has the above stated meaning and Y denotes a group of the formula Y, in which the unoccupied bond line symbolises the bond to the group —COOR" and

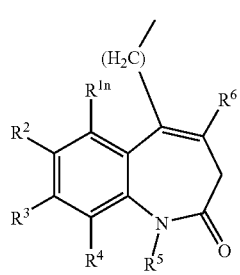

in which R', $R^2$, $R^3$, $R^4$, $R^5$, $R^6$ and n have the above-stated meaning.

F) optionally an ester of the formula Y—COOR" is reacted in the presence of a base, in a suitable solvent, and then worked up, optionally followed by Purification of the carboxylic acid formed of the formula Y—COOH in which Y has the above-stated meaning, G) optionally a carboxylic acid of the formula Y—COOH or a carboxylic acid ester of the formula Y—COOR" in which Y and R" have the above stated meaning, is derivatised in that
  a) a carboxylic acid or carboxylic acid ester of the formula Y—COOH or Y—COOR" is reduced with the assistance of reducing agents, preferably lithium aluminium hydride, in a suitable solvent, preferably tetrahydrofuran, to the corresponding alcohol of the formula Y—$CH_2$—OH,
  b) a carboxylic acid or carboxylic acid ester of the formula Y—COOH or Y—COOR" is reduced with the assistance of reducing agents, in a suitable solvent, to the corresponding aldehyde of the formula Y—CHO or
  c) an alcohol of the formula Y—$CH_2$—OH according to a) is reacted with a brominating agent, to yield the corresponding bromide of the formula Y—$CH_2$—Br and then worked up and the product is optionally purified, H) a compound of the formula $X^1$—$R^{IV}$, in which $X^1$ has the above-stated meaning and $R^{IV}$ denotes a functional group, is optionally produced in that
  a) 1,4-cyclohexanedione monoethylene ketal, 4-oxocyclohexan-1-one ethylene ketal or 4-oxocyclohexane carboxylic acid is reacted with magnesium and a brominated or chlorinated, optionally substituted aromatic or heteroaromatic compound in a suitable solvent, at elevated temperature to yield the corresponding coupling product and then the ketal is optionally cleaved by reaction with hydrochloric acid in a suitable solvent, and worked up, optionally followed by purification of the product of the formula $X^{1a}$=O, $X^{1a}$—$NHR^1$ or $X^{1a}$—$CO_2H$, in which $X^{1a}$ denotes a group of the formula $X^{1a}$ and R1', $R^{2'}$ and Z have the above-stated meaning and the unoccupied bond line symbolises the

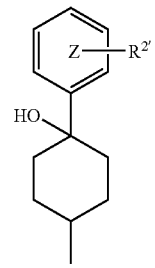

bond to the group =O, —$NHR^{1''}$ or —$CO_2H$,
  b) Optionally a ketone of the formula $X^{1a}$=O is reacted in the presence of a suitable reducing agent, in a suitable solvent, to yield the corresponding alcohol of the formula $X^{1a}$—OH, worked up and the product is optionally purified,
  c) Optionally a ketone of the formula $X^{1a}$=O is reacted under nitrogen in a suitable solvent, firstly with ammonium trifluoroacetate and then with glacial acetic acid and sodium triacetoxy borohydride, to yield the corresponding amine of the formula $X^{1a}$—$NH_2$, worked up and the product is optionally purified, d) optionally a carboxylic acid of the formula $X^{1a}=CO_2H$ is activated by reaction with dicyclohexylcarbodiimide or by conversion into the carboxylic acid chloride or a mixed anhydride, reacted with diazomethane in a suitable solvent, and then treated with water, worked up and the product of the formula $X^{2-}-CO-CH_2-OH$ is optionally purified, e) optionally the hydroxy group in position 4 of the cyclohexane ring in the group $X^{1a}$ is converted into hydrogen, a halogen, an ether, ester, alkyl, or aryl group, in that α) in order to introduce an ether group, a compound from one of steps a)–d) is reacted with an aliphatic or cycloaliphatic compound in the presence of a suitable catalyst in a suitable solvent, or with an alkylating agent in a suitable solvent, or with an aryl compound in the presence of diethylazo dicarboxylate and triphenylphosphine, β) in order to introduce a halogen, a compound from one of steps a)–d) is reacted with a halogenating agent in a suitable solvent, preferably with $POCl_3$ in dimethylformamide, with $PPH_3/Cl_2$, with $PPH_3/Br_2$, with triphenylphosphine/n-chlorosuccinimide or with $HCl/ZnCl_2$, γ) in order to introduce a hydrogen, a compound from step β) is reacted with hydrogen in the presence of a suitable catalyst, in a suitable solvent, δ) in order to introduce an aliphatic or cycloaliphatic or an aryl group, a compound from step δ) is reacted with an aliphatic or cycloaliphatic boronic acid or a boronic acid ester or an aryl or heteroaryl borodihydroxide compound in the presence of palladium(II) acetate and potassium carbonate in a suitable solvent, or ε) in order to introduce an ester group, a compound from one of steps a)–d) is reacted with a carboxylic acid chloride in the presence of a suitable catalyst in a suitable solvent and then worked up, optionally followed by purification of the compound formed of the formula $X^1-R^{IV}$, in which $X^1$ denotes the

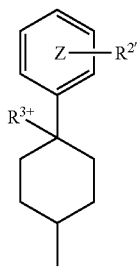

formula $X^1$ and $R^{IV}$, $R^{2\prime}$ and $R^{3\prime}$ have the above-stated meaning, I) a compound of the formula $X-R^{IV}$, in which X has the above-stated meaning and $R^{IV}$ denotes a functional group, is optionally derivatised in that a) a ketone of the formula $X=O$ is reacted 1) with methoxymethyl triphenylphosphine chloride under protective gas in a suitable solvent, preferably in dimethylformamide, in the presence of sodium hydride and then with hydrochloric acid or 2) with $Me_3S-BF_4$ to yield the corresponding aldehyde $X-CHO$ extended by one carbon atom, b) an aldehyde of the formula $X-CHO$ according to a) is reacted with a reducing agent, preferably sodium borohydride, in a suitable solvent, to yield the corresponding alcohol $X-CH_2-OH$, c) an alcohol $X-CH_2-OH$ according to b) or of the formula $X-OH$ is reacted with a brominating agent, in a suitable solvent, preferably acetonitrile, to yield the corresponding bromide of the formula $X-CH_2-Br$ or $X-Br$, d) a bromide of the formula $X-CH_2-Br$ according to c) is reacted with a phosphine of the formula $PR^V_3$, in which $R^V$ denotes an organic group, in a suitable solvent, preferably toluene, ether, tetrahydrofuran or acetone, with cooling and under protective gas to yield the corresponding phosphonium salt $R^V_3P^+-CHX$ or e) a bromide of the formula $X-CH_2-Br$ according to c) is reacted with a phosphite of the formula $HP(O)(OR^{VI})_2$, in which $R^{VI}$ denotes an organic group, at elevated temperature, preferably 200° C., to yield the corresponding phosphonate $(R^{VI}O)_2P(O)-CH_2-X$ and then worked up and the product is optionally purified, J) a compound from step F) or G), in which Y has the above-stated meaning, is reacted with a compound of the formula $X^1-R^{IV}$ from step H) or a compound $X^1-R^{IV}$ from step I), in which X, $X^1$ and $R^{IV}$ have the above-stated meaning, in that a) a carboxylic acid of the formula $Y-COOH$ is reacted with an amine of the formula $X-NH_2$ in the presence of a suitable condensing agent, 1-hydroxybenzotriazole and N-methylmorphine, in a suitable solvent, with formation of an amide bridge, b) a carboxylic acid of the formula $Y-COOH$ is reacted with an alcohol of the formula $X-OH$ in the presence of a suitable condensing agent in a suitable solvent with formation of an ester bridge, the reaction preferably taking place in the presence of methylimidazole and 1-(mesitylene-2'-sulfonyl)-3-nitro-1,2,4-triazole in tetrahydrofuran or in the presence of dicyclohexylcarbodiimide, 1-hydroxybenzotriazole and N-methylmorphine in dimethylformide, c) a bromide of the formula $Y-CH_2-Br$ is reacted with a compound of the formula $X-CO(CH_2)_p-OH$, in which p has the above-stated meaning, under protective gas in the presence of a suitable catalyst, in a suitable solvent, with formation of a bridge of the formula $-CO(CH_2)p-O-CH_2$, d) an alcohol of the formula $Y-CH_2-OH$ is reacted with a bromide of the formula $X-Br$ under protective gas in the presence of a suitable condensing agent, in a suitable solvent, preferably dimethylformamide, with formation of an ether bridge, e) a bromide of the formula $Y-CH_2-Br$ is reacted with an alcohol of the formula $X-OH$ under protective gas in the presence of a suitable condensing agent, in a suitable solvent, preferably dimethylformamide, with formation of an ether bridge, f) an aldehyde of the formula $Y-CHO$ is reacted with an amine of the formula $X-NHR^{1\prime}$ in the presence of a suitable reducing agent, in a suitable solvent, preferably a mixture of tetrahydrofuran and 1,2-dichloroethane, with formation of an amino bridge, g) an aldehyde of the formula $Y-CHO$ is reacted with a phosphonium salt $R''_3P^+-CHX^-$, in which $R''$ has the above-stated meaning, under protective gas in the presence of suitable catalysts in a suitable solvent, preferably in the presence of sodium methanolate in a mixture of hexane, diethyl ether and/or diisopropyl ether or in the presence of sodium hydride, potassium tert-butylate or a lithium amide in dimethylformamide or dimethyl sulfoxide, with formation of a —CH═CH— bridge or h) an aldehyde of the formula Y—CHO is reacted with a phosphonate of the formula $(R'''O)_2P(O)$—$CH_2$—X, in which R''' has the above-stated meaning, under protective gas in the presence of suitable catalysts, preferably sodium methanolate, sodium hydroxide, potassium hydroxide, sodium hydride, potassium tert-butylate or a lithium amide, in a suitable solvent, preferably dimethylformamide, dimethyl, sulfoxide, diethyl ether, tetrahydrofuran, with formation of a —CH═CH— bridge and i) optionally the —CH═CH— bridge from step g) or h) is hydrogenated by hydrogen, preferably at standard pressure or elevated pressure of up to 100 bar, in the presence of suitable catalysts, preferably transition metals or transition metal compounds, preferably palladium or the salts thereof, rhodium or the complexes thereof, in a suitable solvent, preferably dimethylformamide, methanol or ethanol, at a temperature of between 20 and 100° C. with formation of a —$CH_2$—$CH_2$ bridge and then worked up and the product is optionally purified, K) optionally the double bond in the 7-membered ring of one of the reaction products from step I) is hydrogenated by hydrogen, preferably at standard pressure or elevated pressure of up to 100 bar, in the presence of suitable catalysts, preferably transition metals or transition metal compounds, preferably palladium or the salts thereof, rhodium or the complexes thereof, in a suitable solvent, preferably dimethylformamide, methanol or ethanol, at a temperature of between 20 and 100° C. and then worked up and the product is optionally purified.

12. A pharmaceutical preparation containing at least one compound of claim 1 and physiologically acceptable auxiliary substances.

13. A method of treating pain in a patient in need thereof comprising administering to the patient an effective amount of the pharmaceutical preparation according to claim 12.

14. The method according to claim 13 where the pain is selected from chronic pain or neuropathic pain.

15. A compound of claim 1 wherein the compound is in the form of enantiomers or diastereomers, mixtures of the enantiomers or diastereomers, physiologically acceptable salts.

* * * * *